(12) United States Patent
Kentsis et al.

(10) Patent No.: US 9,869,673 B2
(45) Date of Patent: Jan. 16, 2018

(54) DIAGNOSTIC MARKERS AND THERAPEUTIC TARGETS OF KAWASAKI DISEASE

(75) Inventors: Alex Kentsis, New York, NY (US); Susan Kim, Auburndale, MA (US); Hanno Steen, Cambridge, MA (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/111,816

(22) PCT Filed: Apr. 13, 2012

(86) PCT No.: PCT/US2012/033514
§ 371 (c)(1),
(2), (4) Date: Jan. 17, 2014

(87) PCT Pub. No.: WO2012/142409
PCT Pub. Date: Oct. 18, 2012

(65) Prior Publication Data
US 2014/0161791 A1   Jun. 12, 2014

Related U.S. Application Data

(60) Provisional application No. 61/475,936, filed on Apr. 15, 2011, provisional application No. 61/579,007, filed on Dec. 22, 2011.

(51) Int. Cl.
*G01N 33/564* (2006.01)
*G01N 33/68* (2006.01)

(52) U.S. Cl.
CPC ....... *G01N 33/564* (2013.01); *G01N 33/6893* (2013.01); *G01N 2333/47* (2013.01); *G01N 2800/328* (2013.01); *G01N 2800/60* (2013.01)

(58) Field of Classification Search
None
See application file for complete search history.

(56) References Cited

U.S. PATENT DOCUMENTS

| 7,604,936 | B2 * | 10/2009 | Wohlgemuth et al. ...... 435/6.16 |
| 2009/0093005 | A1 | 4/2009 | Smalley et al. |
| 2009/0191575 | A1 | 7/2009 | Watanabe et al. |

FOREIGN PATENT DOCUMENTS

| JP | 2007-205842 | 8/2007 |
| WO | 2007/003594 | 1/2007 |
| WO | 2007/003594 A1 | 1/2007 |
| WO | 2008/021290 | 2/2008 |

OTHER PUBLICATIONS

Ferguson et al (Proteomics 2005, 5, 566-571).*
Adachi et al., Genome Biology, 7:R80 (2006). "The human urinary proteome contains more than 1500 proteins, including a large proportion of membrane proteins."
Chow et al., Zhongua Min Guo Xiao Er Ke Yi Xue Hui Za Zhi, 34(2):77-83 English Abstract (1993). "Serume and urinary interleukin-6 (IL-6) levels as predicting factors of Kawasaki disease activity."
Ebihara et al., Eur J Pediatr, 164:427-431 (2005). "Differential gene expression of S100 protein family in leukocytes from patients with Kawasaki disease."
Kentsis et al., Ann Emerg Med., 55:62-70 (2010). "Discovery and Validation of Urine Markers of Acute Pediatric Appendicitis Using High-Accuracy Mass Spectromerty."
Lin et al., J Pediatr, 121:924-926 (1992). "Serial changes of serum interleukin-6, interleukin-8, and tumor necrosis factor alpha among patients with Kawasaki disease."
Oetting et al., Am J Kidney Dis, 47:898-904 (2006). "Urinary beta2-Microglobulin is Associated With Acute Renal Allograft Rejection."
Peng et al., Zhongguo Dan Dai Er Ke Za Zhi, 8(3):208-210 (2006). "Value of serum soluble interleukin-2R, interleukin-6 and C-reactive protein in the early diagnosis of Kawasaki disease."
Pisitkun et al., Molecular & Cellular Proteomics, 5:1760-1771 (2006). "Discovery of Urinary Biomarkers."
Rai et al., Proteomics, 5:3467-3474 (2005). "Analysis of Human Proteome Organization Plasma Proteome Project (HUPO PP) reference specimens using surface enhanced laser desorption/ionization—time of flight (SELDI-TOF) mass spectrometry: Multi-institution correlation of spectra and identification of biomarkers."
Rowley et al., Nat. Rev. Microbiol., 6:394-400 (2008). "Searching for the cause of Kawasaki disease—cytoplasmic inclusion bodies provide new insight."
Suganami et al., Pediatrics International, 50:264-266 (2008). "Clinical application of rapid assay of serum interleukin-6 in Kawasaki disease."
Woroniecki et al., Am J Nephrol, 26:258-267 (2006). "Urinary Proteome of Steroid Sensitive and Steroid-Resistant Idiopathic Nephrotic Syndrome of Childhood."
Zimmerli et al., Molecular & Cellular Proteomics, 7:290-298 (2008). "Urinary Proteomic Biomarkers in Coronary Artery Disease."
Ebata et al., Circulation Journal, 75(6):1455-1462 (2011). "Increased production of vascular endothelial growth factor-D and lymphangiogenesis in acute Kawasaki disease."
Kaneko et al., Pediatric Cardiology, 32(8):1106-1109 (2011). "Prediction of the risk of coronary arterial lesions in Kawasaki disease by brain natriuretic peptide."

(Continued)

Primary Examiner — Brian Gangle
Assistant Examiner — Andrea K McCollum
(74) Attorney, Agent, or Firm — Nixon Peabody LLP; David S. Resnick; Tari W. Mills

(57) ABSTRACT

The present invention provides for compositions and methods for diagnosing and treating Kawasaki disease. More specifically, the proteomes of patients with KD are enriched for the meprin A, filamin B, and filamin C, which serve as biomarkers (and potential therapeutic targets) for KD. Accordingly, detection of these biomarkers, using compositions and methods provided for herein, can inform the therapy delivered to the subject.

9 Claims, 5 Drawing Sheets

(56) References Cited

OTHER PUBLICATIONS

Huang et al., Pediatric Cardiology, 31(8):1209-1213 (2010). "Acute-phase reactants and a supplemental diagnostic aid for Kawasaki disease."

Saint-Faust et al., Archives de Pediatrie, 14(12):1427-1430 (2007). "Syndrome de Kawasaki chez 1 nourrisson: difficultes diagnostiques et complications liees a l'age."

Bonnemane, C.G., et al., Journal of the Neurological Sciences 206(7):1-78 (2003). "Filamin C accumulation is a strong but non-specific immunohistochemical marker of core formation in muscle."

Walker, P.D., et al., Kidney Internat onaL, vol. 53:1673-1680 (1998). "Meprin A, the major matrix degrading enzyme in renal tubules, produces a novel nidogen fragment in vitro and in vivo."

Shatunov et al. "In-frame deletion in the seventh immunoglobulin-like repeat of filamin C in a family with myofibrillar myopathy", European Journal of Human Genetics, 17(5):656-63 (2009).

\* cited by examiner

DIAGNOSTIC MARKERS AND THERAPEUTIC TARGETS OF KAWASAKI DISEASE

CROSS REFERENCE TO RELATED APPLICATIONS

This application is a 35 U.S.C. §371 National Phase Entry Application of International Application No. PCT/US2012/033514 filed Apr. 13, 2012, which designates the U.S., and which claims benefit under 35 U.S.C. §119(e) of U.S. Provisional Application No. 61/475,936, filed Apr. 15, 2011, and U.S. Provisional Application No. 61/579,007, filed Dec. 22, 2011, the contents of each of which are incorporated fully herein by reference in their entireties.

FEDERAL FUNDING

This invention was made, in part, with Federal funding under grants No. U01 HL068285, RR 02172, U01 HL068270, U01 HL068269, U01 HL068292, U01 HL068290, U01 HL068288, U01 HL068281, and U01 HL068279, awarded by the National Institutes of Health. The U.S. Federal Government has certain rights in the invention.

FIELD

The present invention provides for diagnostic markers and therapeutic targets associated with Kawasaki disease (KD). More specifically, the proteomes of patients with KD are enriched for the meprin A, filamin B, and filamin C, which serve as biomarkers for KD. Accordingly, detection of these biomarkers, using compositions and methods provided for herein, can inform the therapy delivered to the subject.

BACKGROUND

Kawasaki disease (KD) is a systemic vasculitis of unknown etiology. Although Kawasaki disease is the most common cause of acquired pediatric heart disease in the developed world, and remains a major medical problem because its signs and symptoms mimic many other childhood febrile illnesses. The absence of definitive diagnostic markers limits the accuracy of clinical evaluations of suspected KD with significant increases in morbidity. In turn, incomplete understanding of its molecular pathogenesis hinders the identification of rational targets needed to improve therapy.

SUMMARY

The present embodiments provide for markers useful in diagnosing and treating KD. Urine proteomes of patients with KD, but not those with mimicking conditions, were enriched of cellular injury proteins such as filamin and talin, immune regulators such as complement regulator CSMD3, immune pattern recognition receptor muclin, and immune cytokine protease meprin A. Significant elevations of filamin C, filamin B, and meprin A were detected in both the serum and urine in patients with KD. Meprin A, filamin B, and filamin C exhibited superior diagnostic performance as compared with currently used markers of disease in a blinded case-control study. Notably, meprin A was enriched in the coronary artery lesions of a mouse model of KD. In all, urine proteome profiles revealed novel molecular markers of KD, including filamin C, filamin B, and meprin A.

Accordingly, one aspect of the invention provides at least one biomarker specific for the diagnosis and monitoring of KD in a subject in need thereof.

One embodiment of this aspect, provides a urinary and serum biomarker, filamin C, that is significantly elevated in patients with KD.

Another embodiment of this aspect provides a urinary and serum biomarker, meprin A, that is significantly elevated in patients with KD.

Another embodiment of this aspect provides a urinary and serum biomarker, filamin B, that is significantly elevated in patients with KD.

Another embodiment of this aspect provides a panel of biomarkers, each of which is elevated in KD patients, and provides comparative value in the diagnosis and prognosis of KD. In one embodiment of this aspect, the KD biomarker panel comprises, filamin B, filamin C, or meprin A. Such embodiments may also include an agent specific for total protein or a normalizing protein; or an assay to measure the amount or concentration of total protein or a normalizing protein may be performed in order to provide a amount or concentration to which the panel of biomarkers can be normalized, in order to permit various comparisons, for example, between subject samples, or between a series of samples isolated from one subject at different time-points.

In one embodiment of the invention, KD biomarker levels (e.g., quantities or concentrations of filamin C or meprin A) present in a biological sample, such as urine or serum, are measured by contacting the test sample, or preparation thereof, with an agent, such as an antibody-based agent, that specifically binds to at least one KD biomarker, or to a portion thereof, wherein the agent forms a complex with the biomarker which can be used in assays to determine the biomarker level (e.g., quantity or concentration). Any means known to those skilled in art can be used to assess a biomarker level. For example, KD biomarker levels can be assessed by ELISA, multiplex bead assay, or mass spectrometry.

An embodiment provides for an assay for diagnosing KD in a subject comprising analyzing a biological sample obtained from a subject for a level of at least one biomarker, selected from meprin A, filamin B, and filamin C, wherein a >2-fold increase in the level of the biomarker compared with a reference level of a normalizing protein is indicative that the subject KD.

In another aspect, the invention provides methods of optimizing therapeutic efficacy for treatment of KD. Accordingly, in one embodiment of this aspect, the method comprises (a) measuring a level (e.g., quantity or concentration) of at least one biomarker in a panel of biomarkers comprising meprin A, filamin B, or filamin C; and (b) comparing the level of the at least one biomarker with a reference level of the at least one biomarker, wherein an increase in the level of at least one biomarker in a panel of biomarkers comprising meprin A, filamin B, or filamin C in the sample relative to the reference level of said at least one biomarker indicates a need to administer to the subject a therapeutic treatment for KD. In some embodiments, the biological sample is a urine sample. In some embodiments, the biological sample is serum.

In another embodiment of this aspect, the method comprises contacting a biological sample (obtained from a subject) with at least one agent specific for at least one biomarker in a panel of biomarkers comprising at least filamin C, filamin B, or meprin A; (b) measuring an amount or concentration of the at least one biomarker using an assay specific for the at least one agent; and (c) comparing the amount or concentration of the at least one biomarker with a reference level of the at least one biomarker, wherein an increase in the amount or concentration of at least one biomarker in a panel of biomarkers comprising filamin C, filamin B, or meprin A in the sample relative to the reference amount or concentration of said at least one biomarker indicates a need to administer to the subject a therapeutic treatment for KD. In some embodiments, the biological sample is a urine sample. In some embodiments, the biological sample is serum.

In another aspect, the invention provides for kits that comprise means for identifying or measuring at least one KD biomarker, for example, filamin C, filamin B, or meprin A, in a biological sample. The kit comprises a container for holding a biological sample (e.g., urine sample or serum sample), and at least one agent, such as an antibody or portion thereof, that binds specifically at least one KD biomarker for use in determining the amount, concentration or the presence of at least one KD biomarker in a biological sample, such as a urine sample or serum sample.

In one embodiment of this aspect, the kit comprises at least one antibody, or a portion thereof, that specifically binds to at least one KD biomarker and an antibody or portion thereof for immobilization. In one such embodiment, one antibody is immobilized on a solid phase and the at least one antibody specific for at least one biomarker is detectably labeled. The kits can comprise anti-meprin A, anti-filamin B, or anti-filamin C antibodies or portions thereof.

Another aspect relates to a computer readable storage medium having computer readable instructions recorded thereon to define software modules for implementing on a computer a method for diagnosing KD of at least one individual, the computer readable storage medium comprising: (a) instructions for storing and accessing data representing a level of at least one biomarker and a level of a normalizing protein determined for a biological sample obtained from at least one individual; (b) instructions for normalizing the level of the at least one biomarker to the amount of normalizing protein via a normalization module, thereby producing a normalized level of the at least one biomarker, (c) instructions for comparing the normalized level of the at least one biomarker to reference data stored on the storage device using a comparison module, wherein the comparing step produces a retrieved content, and (d) instructions for displaying a page of the retrieved content for the user, wherein the retrieved content displays if there is a change in the normalized level of the at least one biomarker, thereby determining whether the at least one individual has KD. The normalizing protein may be total protein or a specific protein. In one embodiment, the biological sample is a urine sample. In one embodiment, the biological sample is serum.

Also described herein is a computer system for obtaining data from a biological sample obtained from at least one individual, the system comprising: (a) a specimen container to hold a biological sample; (b) a determination module configured to determine reporter molecule information, wherein the reporter molecule information comprises (1) information representing binding of an agent to a normalizing protein, and (2) information representing binding of an agent to at least one biomarker; (c) a storage device configured to store data output from the determination module; (d) a normalization module configured to normalize reporter molecule information representing binding of an agent to at least one biomarker to reporter molecule information representing binding of an agent to normalizing protein; (e) a comparison module adapted to compare the data obtained from the normalization module with reference data on the storage device, wherein the comparison module produces a retrieved content; and (f) a display module for displaying a page of the retrieved content for the user, wherein the retrieved content displays if there is a change in the normalized level of the at least one biomarker, thereby determining whether the at least one individual has KD. In one embodiment, the normalizing protein is specific protein. In one embodiment, the normalizing protein is total protein. In one embodiment, the biological sample is a urine sample. In another embodiment, the biological sample is serum.

DESCRIPTION OF THE DRAWINGS

FIG. 2 illustrates that patients with Kawasaki disease, but not those with mimicking conditions, have significantly elevated serum and urine levels of meprin A and filamin C, which exhibit superior diagnostic performance in a blinded study of patients suspected of KD.

FIGS. 3A-3B: Urine meprin A (FIG. 3A) and filamin C (FIG. 3B) levels in 5 patients with KD, as measured in matched specimens collected at diagnosis, 24-48 hours after treatment, and 1 month after complete clinical response. FIG. 3C: Urine meprin A level in one patient who experienced recurrence of KD 5.5 months after initial presentation. FIG. 3D: Scatter plot showing urine filamin C levels in patients who responded to initial therapy (left, responders) versus those who required repeat treatment (right, non-responders).

FIGS. 4A-4B: Micrographs of hematoxylin and eosin-stained sections of coronary arteries demonstrating infiltrates of mononuclear cells (arrowhead) in KD-moribund (FIG. 4B) but not control (FIG. 4A) animals. FIGS. 4C-4D: Micrographs of meprin A immunohistochemistry-stained sections of coronary arteries demonstrating enrichment of meprin A in mononuclear infiltrates of coronary arteries in moribund (FIG. 4D) but not control (FIG. 4C) animals. FIG. 4E: Serum levels of meprin A are elevated in moribund (right) as compared with control (left) mice.

DETAILED DESCRIPTION

Figure 1:
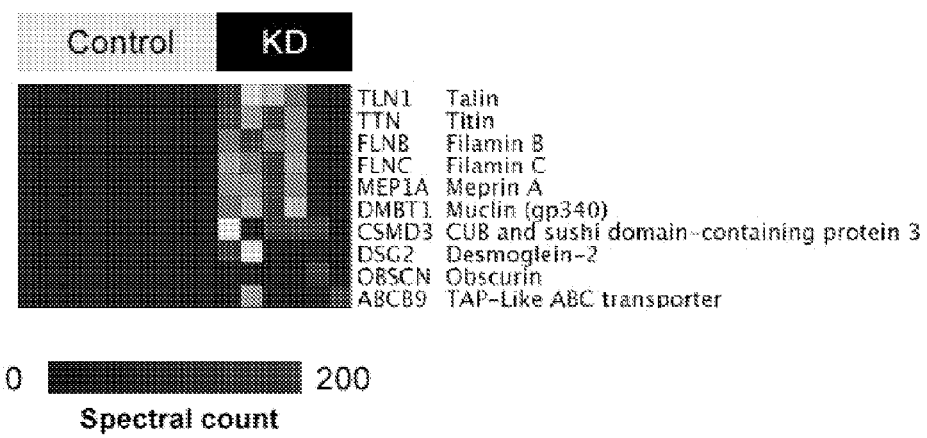
FIG. 1 shows that KD patients exhibit a unique urine proteome that is distinct from patients without KD or with commonly present urinary proteins. Heatmap of the fifteen individual urinary proteomes (columns) showing the results of Bayesian analysis of top ten proteins (rows) that are detected in patients with KD as compared with those without. Shading gradient represents the number of MS/MS spectra (spectral count) that corresponds to urinary protein abundance.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein. The present embodiments provide for novel biomarkers useful for the diagnosis and treatment of KD. Briefly, high-accuracy mass spectrometry proteomics was used to analyze over 2,000 unique proteins in clinical urine specimens of patients with KD. The analysis revealed that urine proteomes of patients with KD, but not those with mimicking conditions, were enriched for markers of cellular injury such as filamin and talin, immune regulators such as complement regulator CSMD3, immune pattern recognition receptor muclin, and immune cytokine protease meprin A. Significant elevations of filamin C and meprin A were detected in both the serum and urine in two independent cohorts of patients with KD, comprised of a total of 192 patients. Meprin A and filamin C exhibited superior diagnostic performance as compared with currently used markers of disease in a blinded case-control study of 69 patients with suspected KD, with receiver operating characteristic areas under the curve of 0.99 (95% confidence interval of 0.96-1) and 0.94 (95% CI of 0.89 to 0.99), respectively.

Notably, meprin A was enriched in the coronary artery lesions of a mouse model of KD. In all, urine proteome profiles revealed novel molecular markers of KD, including filamin C and meprin A. These and other proteins may improve the diagnostic accuracy of clinical evaluations of children with suspected KD, lead to the identification of novel therapeutic targets, and allow the development of a biologic classification of KD.

KD is a systemic vasculitis of unknown etiology that presents with prolonged fever and mucocutaneous inflammation, including inflammation of the oral mucosa, non-exudative conjunctivitis, rash, extremity changes and cervical lymphadenopathy that is usually unilateral. Burns et al., 118 J. Pediatr. 680 (1991). Although Kawasaki disease has an incidence of about 1 in 10,000 in American and European populations, it is the most common cause of acquired pediatric heart disease in the developed world and remains a major medical problem because its signs and symptoms mimic many other childhood febrile illnesses. Baker et al., 154 J. Pediatr. 592 (2009); Taubert et al., 119 J. Pediatr 279 (1991). In addition, the prevalence of KD is particularly high in Asia; 2 in 1,000 Japanese children under the age of 5 years develop Kawasaki disease. Nakamura et al., 20 J. Epidemiol. 302 (2010).

Delays in accurate diagnosis lead to increased mortality and morbidity from complications of KD. Wilder et al., 26 Pediatr. Infect. Dis. J. 256 (2007); Suda et al., 123 Circulation 1836 (2011). In particular, without timely treatment, as many as 25% of patients may develop coronary artery dilatation or aneurysms, with the associated risk of death and long-term morbidity. McCrindle et al., 116 Circulation 174 (2007). Importantly, before the present invention, no pathognomonic test existed for the early identification and diagnosis of KD. Gedalia, 9 Curr. Rheumatol. Rep. 336 (2007); Dedeoglu & Sundel, 33 Rheum. Dis. Clin. N. Am. 555 (2007). The use of clinical algorithms has improved the diagnosis of KD, but their accuracy remains limited. Yellen et al., 125 Pediatrics e234 (2010). Attempts to improve the reliability of clinical evaluations of KD have focused on clinical and general laboratory markers of inflammation. Lin et al., 121 J. Pediatr. 924 (1992); Chow et al., 34 Zhonghua Min Guo Xiao Er Ke Yi Xue Hui Za Zhi 77 (1993); Ebihara et al., 164 Eur. J. Pediatr. 427 (2005); Peng et al., 8 Zhongguo Dang Dai Er Ke Za Zhi 208 (2006); Suganami et al., 50 Pediatr. Int. 264 (2008). Performance is inadequate, however, likely because of the nonspecific relationship in the pathophysiology of KD, which is thought to be caused by an interaction between an infectious trigger and an exaggerated inflammatory response. Rowley et al., 6 Nat. Rev. Microbiol. 394 (2008).

The present embodiments employ a discovery-based approach, which identified KD pathophysiologic alterations on a proteomic scale. Urine was studied because of its abundance and relative analytic simplicity as compared with serum. Previously, high accuracy mass spectrometry measured urine proteomes in sufficient depth to identify local and systemic biomarkers, and to discover improved diagnostic markers of disease. Rai et al., 5 Proteomics 3467 (2005); Pisitkun et al., 5 Mol. Cell. Proteomics 1760 (2006); Adachi et al., 7 Genome Biol. R80 (2006); Woroniecki et al., 26 Am. J. Nephrol. 258 (2006); Oetting et al., 47 Am. J. Kidney Dis. 898 (2006); Zimmerli et al., 7 Mol. Cell. Proteomics 290 (2008); Kentsis et al., 55 Ann. Emerg. Med. 62 (2010).

The present embodiments provide for validated diagnostic markers of KD, identified in a prospective pediatric cohort. High accuracy mass spectrometry proteome profiling of urine specimens collected from children with suspected KD identified the differences in individual urine proteomes. Candidate diagnostic markers were validated in the urine and serum in two independent cohorts of patients with KD using enzyme-linked immunosorbent assays (ELISAs). Their diagnostic performance was then assessed in a blinded, prospective study of children with suspected KD.

The initial subject study enrolled sixty-nine subjects, who presented with fever and concern for possible KD. In agreement with previous studies of the epidemiology and presentation of KD, the study population was predominantly male, with a mean age of 3 years and with the presenting signs and symptoms described in Table 1:

TABLE 1

Presenting signs, symptoms, diagnostics of patients with suspected KD

| | Final Diagnosis | |
| --- | --- | --- |
| Characteristic | KD | Non-KD |
| Total | 45 | 24 |
| Gender (% male) | 78 | 56 |
| Race (%) | | |
| Caucasian | 68 | 68 |
| African American | 20 | 16 |
| Asian | 9 | 8 |
| Age, years | 3.3 ± 2.5 | 4.6 ± 2.4 |
| Duration of fever, days | 6.4 ± 2.2 | 6.3 ± 1.8 |
| Number of primary criteria* | 4 (3-5) | 2 (1-4) |
| Conjunctivitis, % | 97 | 52 |
| Mucositis, % | 91 | 44 |
| Rash, % | 91 | 44 |
| Extremity changes, % | 75 | 32 |
| Lymphadenopathy, % | 53 | 28 |
| Pyuria, % | 31 | 12 |
| Peripheral WBC, K cells/mm$^3$ | 14.6 ± 4.4 | 9.8 ± 3.7 |
| Hgb, g/dl | 10.4 ± 1.9 | 10.8 ± 2.2 |
| Platelet, K cells/mm$^3$ | 434.4 ± 138.5 | 304.2 ± 122.9 |
| Na (mmol/L) | 134 ± 3 | 135 ± 2.8 |
| CRP (mg/dL) | 11.2 ± 7.4 | 7.8 ± 7.2 |
| ESR (mm/hour) | 79.8 ± 26 | 49.8 ± 23.5 |
| ALT (unit/L) | 76.4 ± 117.2 | 31.2 ± 35.2 |
| Albumin (g/dL) | 3.4 ± 0.4 | 3.7 ± 0.4 |
| Incomplete presentation[†], % | 8/44 (18%) | |

Values are reported as mean ± standard deviation, where appropriate, except for the number of criteria, which is reported as median (range).
*Primary criteria: fever ≥5 days, conjunctivitis, oropharyngeal findings, rash, extremity changes, adenopathy.
[†]Incomplete presentation (see text for description); Hgb, hemoglobin; Na, sodium; CRP, C-reactive protein; ESR, erythrocyte sedimentation rate; ALT, alanine aminotransferase. Pyuria was defined as having >10 white blood cells/high-powered field.

Forty five patients (65%) were ultimately diagnosed with KD. All patients with KD received treatment with high-dose aspirin and intravenous gammaglobulin, with thirteen patients (28%) requiring repeat treatment due to lack of initial clinical response. One patient (2%) initially responded to therapy, but developed recurrent disease 6 months following initial presentation. Twelve of twenty-four patients without KD (50%) were found to have non-specific viral syndrome, with the remaining patients found to have a variety of conditions that may mimic KD, as shown in Table 2:

TABLE 2

Final diagnosis of the 69 study patients

| Final diagnosis | Number of patients |
| --- | --- |
| Kawasaki disease | 45 |
| Viral syndrome | 12 |
| Adenovirus | 5 |

TABLE 2-continued

Final diagnosis of the 69 study patients

| Final diagnosis | Number of patients |
| --- | --- |
| Pyelonephritis | 2 |
| Serum sickness | 2 |
| Osteomyelitis | 1 |
| Lyme disease | 1 |
| Cytomegalovirus | 1 |

Candidate diagnostic markers of KD were identified based on the analysis of fifteen specimens collected at the onset of the study and chosen based on availability: six KD specimens (three without and three with coronary artery dilatation), six non-KD specimens (two with non-specific viral syndromes, 3 with adenovirus, and 1 with pyelonephritis), and 3 matched specimens collected from patients with KD one month following complete response to treatment (convalescent KD). This analysis showed the tissue and physical origin of the aggregate urine proteomes similar to previous studies (Kentsis et al., 3 Proteomics Clin. Appl. 1052 (2009)), and identified 2,131 unique proteins. Analysis of the three comparison groups led to the identification of more than 190 proteins in the urine of patients with KD, but not in any of the patients without KD or in those in which KD had resolved completely. The abundance of candidate KD markers was analyzed to identify those that are most enriched in patients with KD, ranking them in order of relative abundance and prevalence (FIG. 1). The identified markers include a variety of proteins associated with endothelial and myocardial cell injury such as filamin and titin, and immune regulators such as DMBT1 and meprin A.

Selected candidate KD markers using commercially available ELISAs, were validated analyzing the urine levels of filamin C and meprin A. The KD diagnostic performance of filamin C and meprin A was assessed by measuring their concentrations in the urine of patients, with investigators blinded to the patients' final diagnosis. Urine concentrations of both meprin A and filamin C were significantly elevated in patients with KD as compared with those without (mean filamin C of 21.7 versus 3.8 ng/ml, and mean meprin A of 57.1 versus 12.4 ng/ml, respectively, p<0.05, FIGS. 2A-2B), Table S2:

TABLE S2

Meprin A and Filamin C are significantly elevated in urine of patients with KD

| Urine Marker | Non-Kawasaki disease, n = 25 | Kawasaki Disease, n = 44 |
| --- | --- | --- |
| Filamin C (ng/ml) | 3.8 ± 3.4[a,b] | 21.7 ± 18.2 |
| Meprin A (ng/ml) | 12.4 ± 4.4[a,b] | 57.1 ± 20.9 |

Values in table represent mean ± standard deviation of untransformed measurements; statistical comparisons were carried out using analyses of log-transformed measurements.
[a]p < 0.05 versus Kawasaki disease group,
[b]p < 0.05 versus Kawasaki disease group.

Controlling for age, sex, race and duration of fever did not affect the statistical significance of the elevations of meprin A and filamin C. Notably, urine meprin A and filamin C were also significantly elevated in patients with incomplete presentations of KD, meeting only three of the four conventional major diagnostic criteria, as compared with those without KD (mean filamin C of 28.5 ng/ml versus 3.8 ng/ml, and mean meprin A of 38.2 ng/ml vs. 12.4 ng/ml, respectively, both p<0.05).

Figures 2A, 2B, 2C:
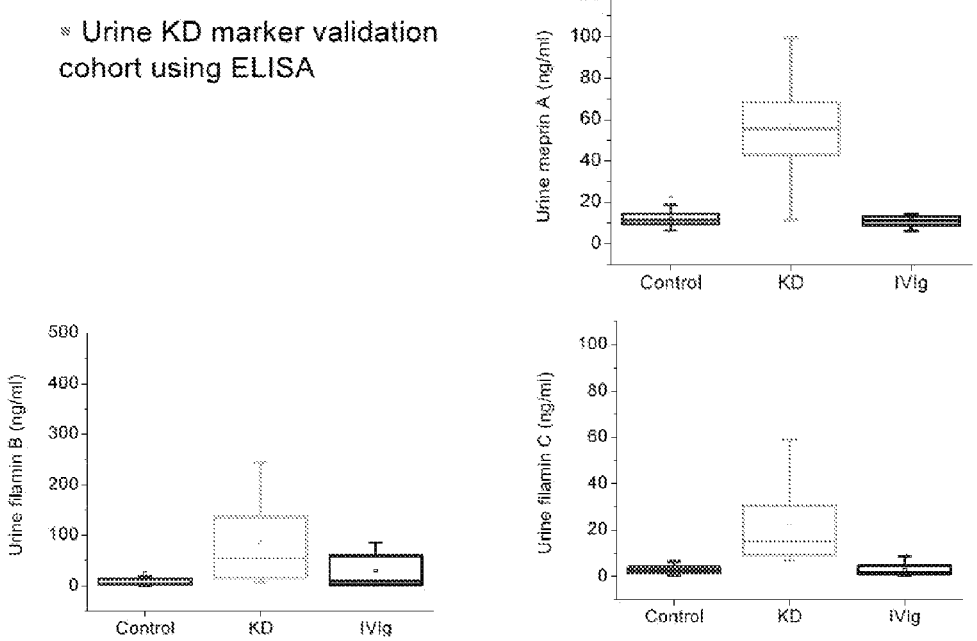
FIGS. 2A-2C: Box plots of urine concentrations measured using specific ELISAs of meprin A, filamin B, and filamin C in a blinded case-control study of patients suspected of KD, demonstrating significantly elevated concentrations of meprin A and filamin C in patients with KD (center) as compared with those with non-KD conditions (left) and patients with KD upon receiving intravenous gammaglobulin treatment (IVIg, right). $P<0.05$. Horizontal bars represent means for each comparison group.
Figure 2D:
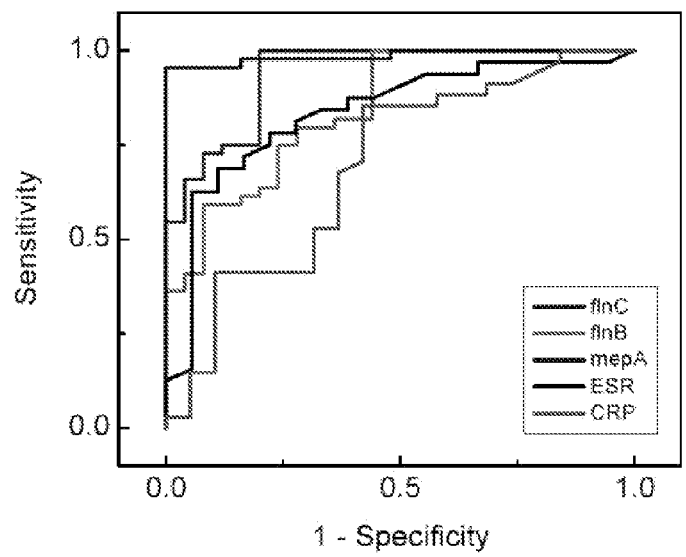
FIG. 2D: Receiver operating characteristics of urine meprin A (first left line), filamin B (second left line) and filamin C (fourth left line), as compared with common markers, erythrocyte sedimentation rate (ESR, third left line) and serum C-reactive protein (CRP, right line). Receiver operating characteristic area under the curve (AUC) values and their 95% confidence intervals (CI) for the measured diagnostic markers.
Figure 5:
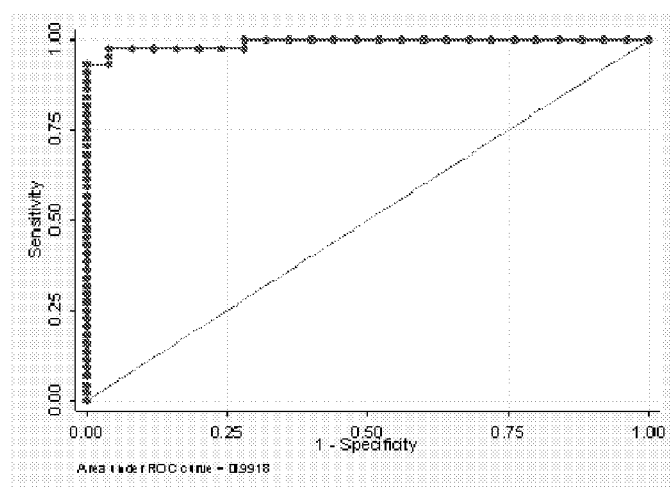
FIG. 5 presents a data reflecting the diagnostic performance of meprin A and filamin C, combined, using receiver operating characteristic (ROC) analysis. Use of these dual KD biomarkers provides for a high level of sensitivity and specificity in KD diagnosis.

The diagnostic performance of meprin A and filamin C was analyzed for all sixty-nine patients using receiver operating characteristic (ROC) analysis. The ROC curves for these markers exhibited superior diagnostic performance as compared with the currently used laboratory markers such as the erythrocyte sedimentation rate (ESR) and C-reactive protein (CRP), with meprin A and filamin C having an area under the curve value of 0.99 (95% CI of 0.96–1.0) and 0.94 (95% CI of 0.89 to 0.99), respectively (FIGS. 2C-2D, 5).

The relationship between meprin A and filamin C and response to therapy was assessed by measuring their urine concentrations in matched serial specimens. These were collected at diagnosis prior to initiation of therapy, 24-48 hours after treatment with high dose aspirin and intravenous gammaglobulin, and 1 month after complete clinical response to treatment in five patients for whom matched specimens could be collected. In all patients studied, urine meprin A and filamin C levels correlated with response to treatment (one-way ANOVA $p<0.05$, FIGS. 3A-3B).

In particular, urine meprin A was un-measurable in one patient with KD, who initially responded to treatment but whose disease recurred 5.5 months after initial presentation. Recurrent elevation of urine meprin A was associated with the relapse of KD (FIG. 3C). Likewise, patients who required repeat treatment with intravenous gammaglobulin, due to the lack of initial clinical response, had significantly higher amounts of filamin C at presentation than patients who responded to initial therapy (mean 64 versus 20 ng/ml, $p<0.05$, FIG. 3D).

Figures 2E, 2F:
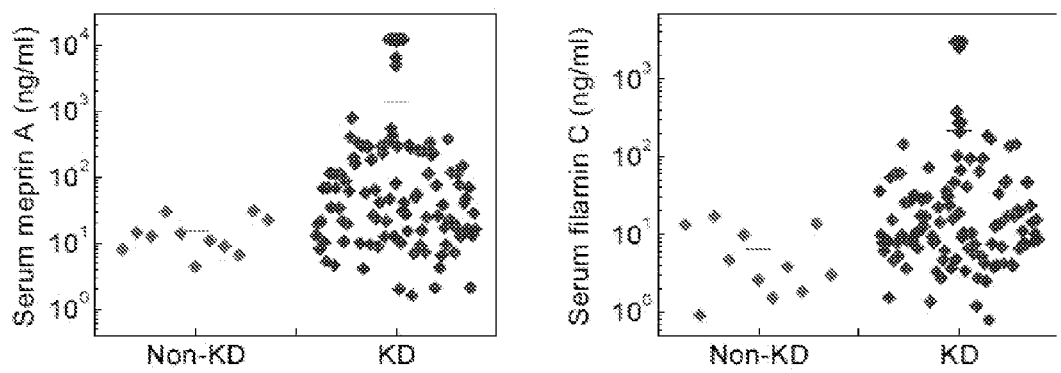
FIGS. 2E-2F: Box plots of serum concentrations measured using specific ELISAs of meprin A (FIG. 2E) and filamin C (FIG. 2F) in patients with KD (right) as compared to patients with non-KD mimicking conditions (left). $p<0.05$.

Encouraged by these findings, the validation of meprin A and filamin C was extended to an independent cohort of patients. Thus, 112 serum specimens of patients with KD were analyzed (collected as part of the recent Pediatric Heart Network study), and compared with eleven patients initially suspected to have KD but ultimately diagnosed with non-KD febrile illnesses (FIGS. 2E-2F). Using ELISAs, both meprin A and filamin C were significantly elevated in the serum of patients with KD as compared with non-KD controls (mean filamin C of 217 versus 6.6 ng/ml, and mean meprin A of 1,363 versus 14.8 ng/ml, respectively, both $p<0.05$), Table S3:

TABLE S3

Meprin A and Filamin C are significantly elevated in serum of patients with KD

| Serum Marker | Non-Kawasaki disease, n = 11 | Kawasaki disease, n = 112 |
| --- | --- | --- |
| Filamin C (ng/ml) | 6.6 ± 5.8[a,b] | 216.6 ± 707.8 |
| Meprin A (ng/ml) | 14.8 ± 9.1[a,b] | 1362.8 ± 3587.1 |

Values in table represent mean ± standard deviation of untransformed measurements; statistical comparisons were carried out using analyses of log-transformed measurements.
[a] $p < 0.05$ versus Kawasaki disease group,
[b] $p < 0.05$ versus Kawasaki disease group.

Figure 6:
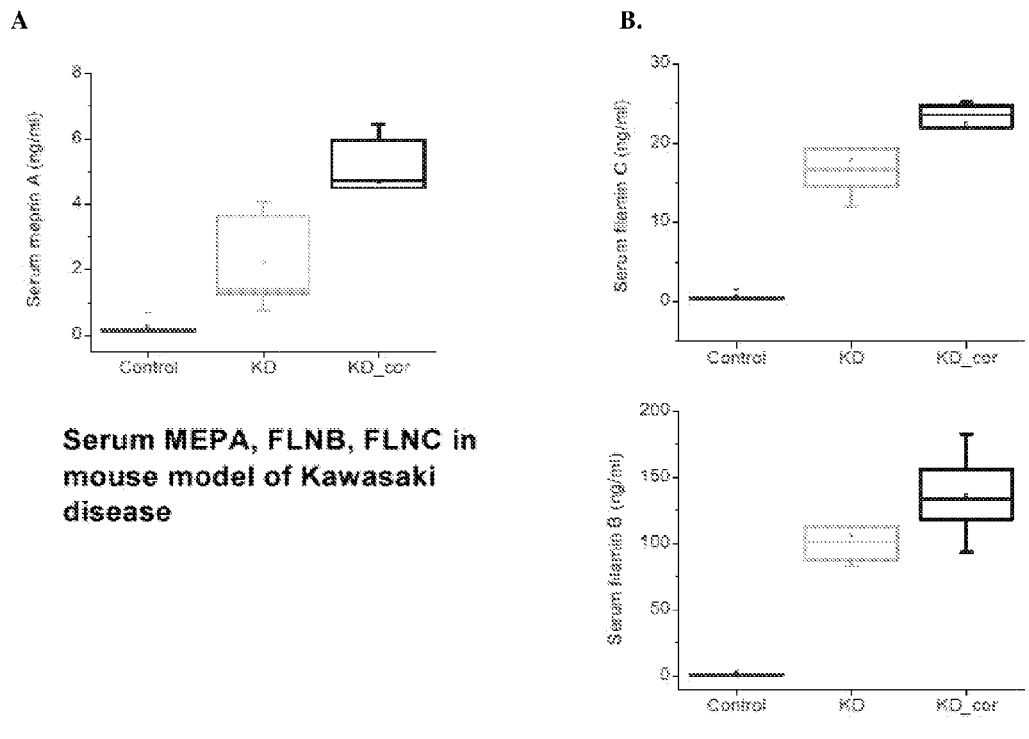
FIGS. 6A-C show data comparing serum levels of meprin A, filamin B, and filamin C in a mouse model of KD.

Because meprin A is a protease that regulates a variety of immune cytokines, the potential involvement of meprin A in the pathogenesis of KD was investigated, using a mouse model of coronary arteritis that reproduces several features of KD. Lehman et al., 48 Clin. Immunol. Immunopathol. 108 (1988). In this model, moribund mice develop systemic mononuclear vasculitis that leads to coronary artery aneurysms. Immunohistochemical analysis using specific meprin A antibodies showed that meprin A was enriched in the vascular lesions of mice with coronary arteritis, but not in control mice (FIGS. 4A-4D). Likewise, levels of circulating meprin A were significantly elevated in the serum of mice with coronary arteritis as compared with control mice (mean 4.7 versus 0.3 ng/ml, $p<0.05$, FIG. 4E). See also FIG. 6.

KD, an acute idiopathic vasculitis of children, causes significant morbidity and mortality if not diagnosed and treated expeditiously. The use of clinical algorithms in combination with echocardiography has improved the accuracy of diagnostic evaluations of KD. In conjunction with prompt treatment, this has led to significant reductions in mortality and complications from coronary aneurysms. Before the present invention, however, major diagnostic challenges remained because the clinical criteria used to diagnose KD are not specific for this condition, and a significant subset of children with KD lack several of the cardinal manifestations of the disease (incomplete KD).

Several earlier studies have sought to identify biomarkers of KD, with the goal of improving the diagnostic accuracy of evaluations of possible KD. Acute phase reactants such as peripheral blood white cell count, ESR and CRP levels are the most clinically useful. These markers remain inadequate in terms of their specificity and sensitivity (Xiu-Yu et al., 24 J. Clin. Lab. Anal. 385 (2010); Huang et al., 31 Pediatr. Cardiol. 1209 (2010)), as confirmed herein (FIGS. 2C-2D). Recent attempts to identify improved diagnostic markers, such as osteoprotegerin, natriuretic peptide, and vascular endothelial growth factor also produced limited improvements, likely as a result of insufficient specificity for the distinct immune mechanisms that characterize KD. Simonini et al., 32 J. Rheumatol. 2233 (2005); Kaneko et al., Pediatr Cardiol, (2011); Ebata et al., 75 Circ. J. 1455 (2011).

The high accuracy and sensitivity of recently developed mass spectrometry approaches facilitated discovery of the novel, more accurate and sensitive diagnostic markers described herein. The urine proteomes of patients with KD as compared with those initially suspected to have KD but ultimately proved to have other febrile illnesses, allowed construction of a molecular pathophysiologic profile of KD comprised of over 190 unique candidate KD markers (FIG. 1). These molecules include markers of endothelial and myocardial injury (talin, filamin, desmoglein, obscurin, titin), leukocyte activation (AMICA1, CAECAM, CXCL12, GDF15, LAIR1), pathogen immune recognition (DMBT1, ABCB9), and cytokine regulation (CSMD3, meprin A).

As provided herein, several immune regulatory molecules to be uniquely present in the urine of patients with KD. Among these was meprin A, a metalloprotease that functions in the activation and degradation of inflammatory cytokines which have been implicated in the pathogenesis of KD, including IL-1 and IL-6. Chow et al., 1993; Herzog et al., 31 Cytokine 394 (2005). Similarly, DMBT1, also known as muclin or gp340, is an innate immune scavenger receptor that recognizes a variety of bacterial and viral antigens. Madsen et al., 16 Innate Immunol. 160 (2010). Finally, ABCB9, also known as TAPL, is a transporter that functions in immune antigen presentation. Bangert et al., 392 Biol. Chem. 61 (2011). Many of the identified KD markers, if properly validated as we have done here, may represent not only diagnostic markers, but also novel therapeutic targets. In all, the identified proteomes, available at the Proteome Commons (on-line at proteomecommons.org), and containing 190 novel candidate KD markers, listed in Table S1, provide a molecular physiologic profile of KD. Interactions of the components of the innate and adaptive immune responses in patients implicated by this molecular profile may further elucidate pathogenic mechanisms mediating KD.

Importantly, this prospective, blinded study of patients with suspected KD, confirmed that filamin C and meprin A are significantly elevated in the serum and urine of patients with KD but not those with a variety of mimicking conditions (FIG. 2). Both markers demonstrated superior diagnostic performance as compared with the currently used laboratory tests (FIG. 2). Filamin C's predominant expression in myocytes suggests that filamin C represents a sensitive and specific marker of the subclinical myocarditis that accompanies KD. Indeed, markers of frank cardiomyocyte injury such as troponin have not been found to correlate with clinical or echocardiographic evidence of myocarditis. Checchia et al., 22 Pediatr. Cardiol. 102 (2001); Sato et al., Intl. J. Cardiol. (Jul. 19, 2011). In addition, elevated levels of filamin C in patients with KD who did not respond to initial therapy as compared with those with complete response suggest that filamin C is a marker of KD activity (FIG. 3D).

Figure 3:
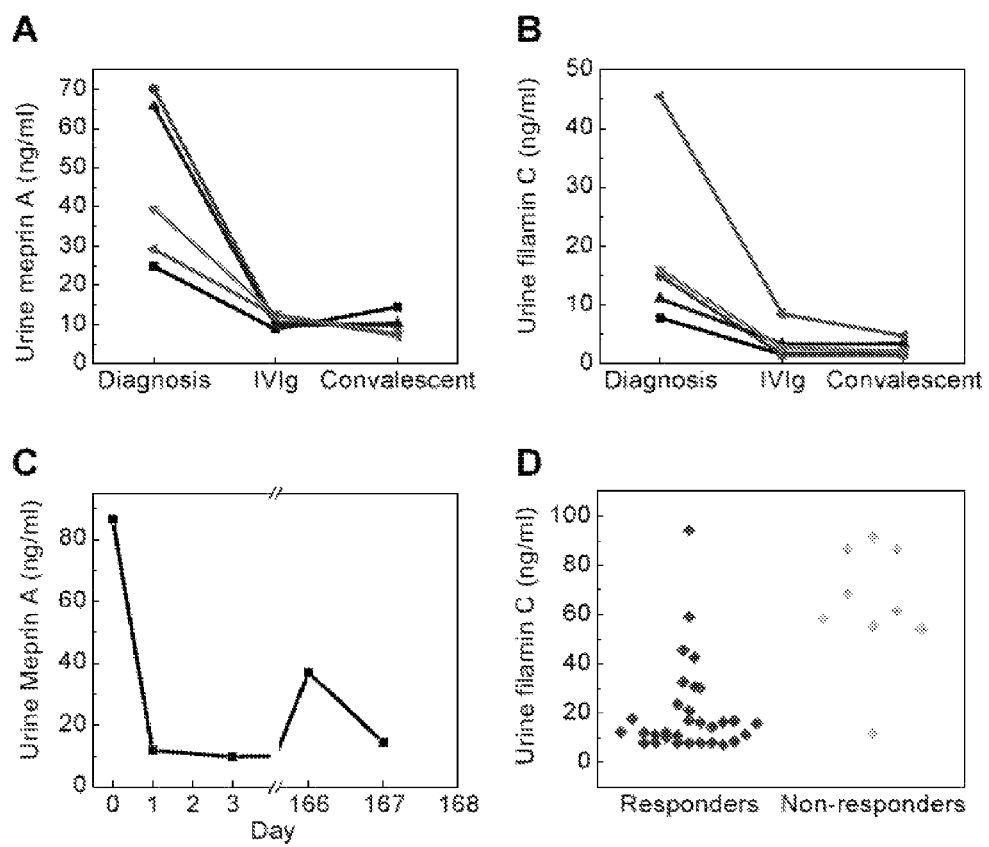
FIG. 3 shows urine filamin C and meprin A correlated with disease activity in patients with KD.
Figure 4:
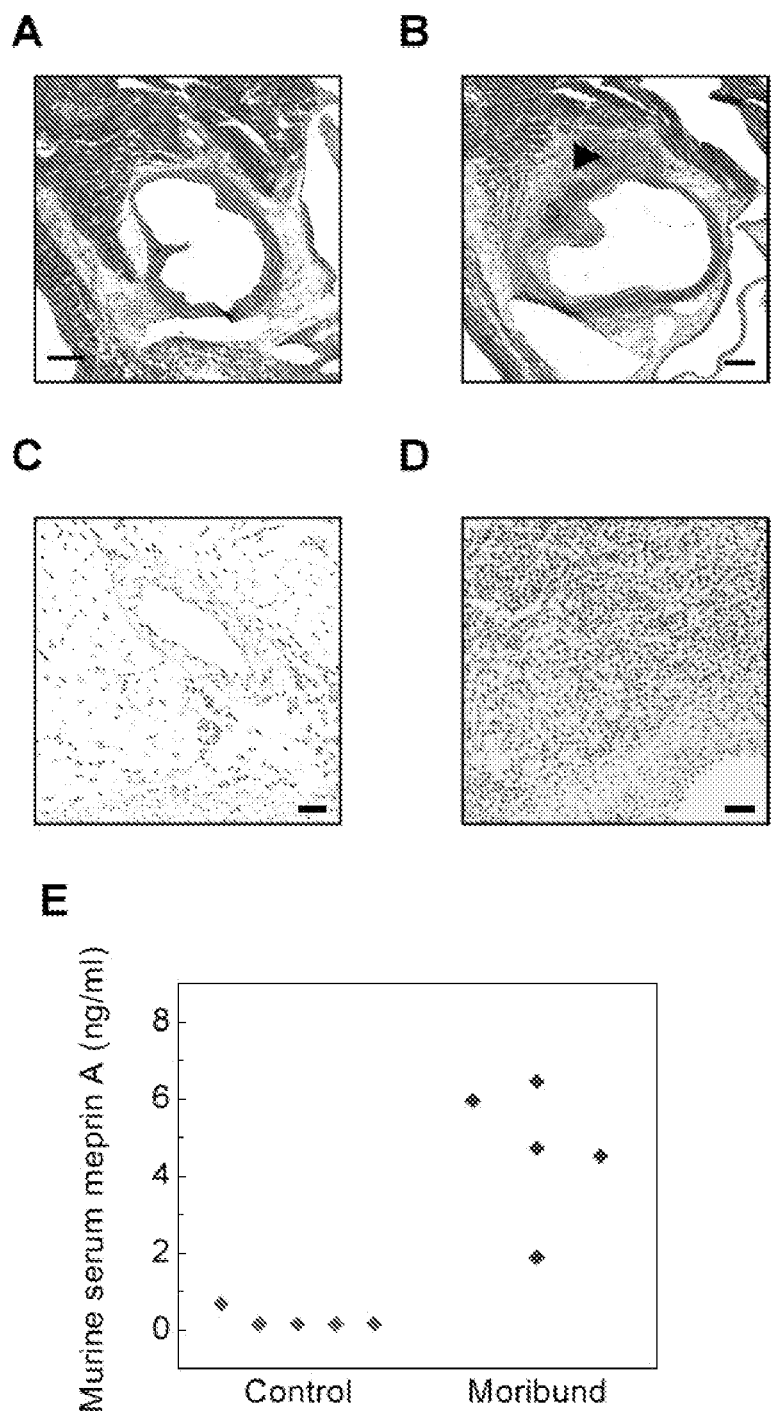
FIG. 4 shows that meprin A is enriched in coronary artery lesions in a mouse model of Kawasaki disease.

Similarly, meprin A is a protease that regulates a variety of inflammatory cytokines, including biologically active IL-1β, a key pro-inflammatory cytokine (Herzog et al., (2005), polymorphisms of which have been associated with resistance to treatment of KD (Weng et al., 74 Circ. J. 544 (2010)). Thus, meprin A may contribute to the initiation, propagation or compensatory immune mechanisms of KD. The potential contributions of meprin A to the pathophysiology of KD are emphasized by its enrichment in the coronary lesions in a mouse model of KD (FIG. 4) and correlation with disease activity in patients with KD (FIG. 3).

The mechanisms by which these discovered KD markers accumulate in urine of patients and their relationship to the pathophysiology of KD offer immediate utility for the present embodiments. In addition, the presently discovered urine protein markers may have clinical relevance in patients with renal or urologic disease or extreme dehydration. More broadly, the approach presented here advances a proteomic profiling paradigm designed specifically for direct translation to clinical practice, with applications in a wide variety of common and rare human conditions. See, e.g., Kentsis et al., 3 Proteomics Clin. Appl. 1052 (2009); Kentsis, 55 Annals Emerg. Med. 62 (2010).

In sum, the work presented here opens many potential approaches for improving the diagnosis of KD, elucidating its pathophysiology, and directing therapy. In particular, the validation of meprin A, filamin B, and filamin C as specific and sensitive markers of KD, as provided herein, enables their clinical use, e.g., in commonly available ELISAs, to improve the accuracy and timeliness of diagnosis of KD. In addition, the described molecular physiologic profiles and validated diagnostic markers of the present invention now allow for a biologic classification of KD that will improve patient stratification and allow for individualized treatment.

Accordingly, one aspect of the invention provides at least one biomarker specific for the diagnosis and monitoring of KD in a subject in need thereof. One embodiment of this aspect provides a urinary and serum biomarker, filamin C, that is significantly elevated in patients with KD. Another embodiment of this aspect provides a urinary and serum biomarker, meprin A, that is significantly elevated in patients with KD. Another embodiment of this aspect provides a urinary and serum biomarker, filamin B, that is significantly elevated in patients with KD.

The terms "individual", "subject", and "patient" are used interchangeably and refer to an animal, for example a mammal, such as a human. The term "mammal" includes humans, non-human primates (e.g., apes, monkeys), dogs, cats, horses, cattle, pigs, rats, hamsters, Guinea pigs, and mice.

The terms "sample" or "biological sample" refers to a sample of biological fluid, tissue, or cells, in a healthy or pathological state obtained from a subject. Such samples include, but are not limited to, urine, whole blood, serum, plasma, sputum, saliva, amniotic fluid, lymph fluid, tissue or fine needle biopsy samples, peritoneal fluid, cerebrospinal fluid, and includes supernatant from cell lysates, lysed cells, cellular extracts, and nuclear extracts. In some embodiments, the whole blood sample is further processed into serum or plasma samples. In some embodiments, a sample is taken from a human subject, and in alternative embodiments the sample is taken from a mammal. The sample can be pretreated as necessary for storage or preservation, by dilution in an appropriate buffer solution or concentrated, if desired. Any of a number of standard aqueous buffer solutions, employing one of a variety of buffers, such as phosphate, Tris, or the like, at physiological pH can be used. The sample can be stored for use prior to use in the assays as disclosed herein. Storage can be at +4° C. or frozen, e.g., at −20° C. or −80° C.

"Biomarker", "urinary biomarker", or "serum biomarker" refers to a protein or polypeptide expressed endogenously in an individual or found or sequestered in a biological sample from an individual. The term "KD biomarker" is used throughout the specification as an example of a type of biomarker useful with the methods described herein. A KD biomarker refers to at least one of meprin A, filamin B, or filamin C. For each of the biomarkers useful for diagnosing KD, e.g., meprin A, filamin B, or filamin C, a reference to the biomarker protein also encompasses domains or fragments of those proteins, as well as species, variants, homologs, allelic forms, mutant forms, and equivalents thereof.

"Agent" can refer to a protein-binding agent that permits detection or quantification of levels, concentrations, expression levels, or activity of the total protein in a biological sample, a normalizing protein (e.g., actin), or a KD biomarker in a sample, such as a biological sample. Such agents include, but are not limited to, antibodies ("antibodies" includes portions of antibodies such as epitope- or antigen-binding peptides, paratopes, functional CDRs; recombinant antibodies; chimeric antibodies; tribodies; midibodies; or derivatives, analogs, variants, portions, or fragments thereof), protein-binding agents, small molecules, recombinant protein, peptides, aptamers, avimers and protein-binding derivatives, portions or fragments thereof. The phrase "agent specific for at least one biomarker" refers to a biomarker-binding agent that directly of indirectly permits detection or quantification of levels, quantities, concentrations or expression levels for a biomarker. Such agents include, but are not limited to, antibodies or portions thereof, protein-binding agents, small molecules, recombinant protein, peptides, aptamers, avimers and protein-binding derivatives or fragments thereof. An agent upon binding a specific biomarker, normalizing protein, or total protein forms an "agent-biomarker complex," "agent-normalizing protein complex," or "agent-total protein complex."

"Reporter molecule information" refers to data derived from a signal indicating binding of an agent to, or complex formation with, a KD biomarker in a sample, i.e., formation of an "agent-biomarker complex," "agent-normalizing protein complex," or "agent-total protein complex." A signal can comprise, e.g., light, fluorescence, colorimetric or other detectable signal that indicates agent binding to a KD biomarker, a normalizing protein, or total protein.

The phrase "an increase in the level of at least one biomarker over the level of normalizing protein" refers to a level (e.g., concentration or quantity) of at least one biomarker that is greater than a level of a normalizing protein present in a biological sample or reference level. The terms "increased concentration", "increase in the level", "higher level", or "higher concentration" of a biomarker refers to a level of a biomarker that is statistically significant or significantly above the level of that biomarker found in a control or reference sample, in a sample from the same subject at a different time-point, relative to the level of a normalizing protein, or relative to a reference level. The phrase "an increase in the level of at least one biomarker over the concentration of normalizing protein" refers to a concentration or amount of at least one biomarker that is greater than a concentration or amount of a normalizing protein present in a biological sample. The "higher level" or "increase in the level" can be for example 1.2-fold or higher, for example, at least 1.8-fold higher, at least 1.9-fold higher, at least 2-fold higher (i.e., ≥2-fold), at least 3-fold higher, at least 4-fold higher, etc., inclusive. Similarly, an AUC value of about 0.78 may be considered statistically significant. For purposes of comparison, the test sample and control sample are from the same sample type; that is, obtained from the same biological source (e.g., urine or serum). The control or reference sample can also be a standard sample that contains the same concentration of the KD biomarker that is normally found in a biological sample that is obtained from a healthy individual. Alternatively, the control may be a normalizing protein found in the biological sample of the patient that may be used to normalize the KD biomarkers.

In one embodiment, the term "higher level" or "increase in the level" of the biomarker refers to an increase in the level of at least one biomarker in a sample from a subject, of at least 5% compared to a reference value or a normalizing protein value. An increase in the level of a biomarker may be at least 10%, at least 15%, at least 20%, at least 35%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, inclusive; at least 1-fold, at least 1.2-fold, at least 1.8-fold, at least 1.9-fold, at least 2-fold (i.e., ≥2-fold), at least 3-fold, at least 5-fold, at least 10-fold, at least 25-fold, at least 50-fold, at least 100-fold, at least 1000-fold or more, inclusive, higher than a reference level (for example, the level of the same biomarker in a sample from an individual not having KD).

In another embodiment, a decrease in the level of at least one biomarker is at least 20%, at least 30%, at least 40%, at least 50%, at least 60%, at least 70%, at least 80%, at least 90%, at least 95%, at least 99%, or even 100%, (i.e., absent), inclusive, compared with a reference level. In an alternate embodiment, the "difference in the normalized level" refers to a statistically significant change (either an increase or decrease) in level of at least one biomarker compared with a reference level.

"Normalizing the level of the biomarker" and the like refers to the conversion of a data value representing the level of a biomarker (e.g., filamin B, filamin C, or meprin A) in a sample by dividing it by the expression data value representing the level of total protein or a normalizing protein in the sample, thereby permitting comparison of normalized biomarker values among a plurality of samples, or to one or more reference samples or reference values.

"Normalizing protein" or "normalizing factor," refers to a protein against which the levels of a biomarker of interest are normalized to, to permit comparison of amounts of the protein of interest in different biological samples. In some embodiments, the different biological samples are from different subjects. In other embodiments, the different biological samples are from the same subject, but after different time-points. Generally, a normalizing protein is constitutively expressed and is not differentially regulated between at least two physiological states or conditions from which samples will be analyzed, e.g., given disease and non-disease states. Thus, for example, a normalizing protein does not vary substantially (i.e., <15%, <10%, <7%, <5%, <4%, <3%, <2%, <1% or less, inclusive) in the presence and absence of disease, e.g., KD. In one embodiment, a normalizing protein is selected based on the degree of correlation (e.g., lowest amount of scatter or lowest standard deviation among replicates) of the protein measured over a series of sample dilutions, compared to the predicted relationship of the dilution series (e.g., predicted by linear regression). For example, a normalizing protein can be selected that has the highest degree of correlation (e.g., as compared to another protein in a protein sample subjected to the same measurement) for measured protein levels assessed over the dilution series. "Highest degree of correlation" refers to a standard deviation for protein measurements (e.g., replicate measurements) over a dilution series of <2 compared with the predicted relationship over the dilution series; preferably the standard deviation is <1.5, <1, <0.5, <0.1, <0.01, <0.001 or less, inclusive, including a standard deviation of zero (e.g., measured and predicted values are the same). In some embodiments, the normalizing protein is the product of a "housekeeping gene:" a gene encoding a protein that is constitutively expressed, and is necessary for basic maintenance and essential cellular functions. A housekeeping gene generally is not expressed in a cell- or tissue-dependent manner, most often being expressed by all cells in a given organism. Some examples of normalizing proteins encoded by housekeeping genes include, e.g., actin, tubulin, GAPDH, among others. In one embodiment, a housekeeping gene product is used as a normalizing protein.

A variety of assay formats that can be used to determine the level of a biomarker or a normalizing protein. Examples of assay formats include known techniques such as Western blot analysis, radioimmunoassay (RIA), Immunoradiometric assay (IRMA), chemiluminescent immunoassays, such as enzyme-linked immunosorbent assay (ELISA), multiplex bead assays, a fluorescence antibody method, passive haemagglutination, mass spectrometry (such as MALDI/TOF (time-of-flight), SELDI/TOF), liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectroscopy, and HPLC-tandem mass spectrometry (HPLC-MS/MS). Some of the immunoassays can be easily automated by the use of appropriate instruments such as the Siemens Bayer ACS180™ Chemistry Analyzer (available widely, e.g., from Block Scientific., Inc., Bohemia, N.Y.) for a chemiluminescent immunoassay.

RIA and ELISA provide the benefit of detection sensitivity, rapidity, accuracy, possible automation of procedures, and the like, for the determination of the concentration or level of a biomarker. See generally, Kazi et al., 13 J. Coll. Physicians Surg. Pak 22 (2003); Ohkuni et al., 1289 Intl. Cong. Ser. 71 (2006); Mitchell et al., 5 Mol. Microbiol. 1883 (1991); Kashyap et al., 60 J. Clin. Invest. 171 (1977). Antibody arrays or protein chips can also be employed. See, e.g., U.S. Patent Application Pubs. No. 2003/0013208, No. 2002/0155493, No. 2003/0017515; U.S. Pat. No. 6,329,209, U.S. Pat. No. 6,365,418. Other techniques can be used to detect the KD biomarkers described herein as required to practice the methods described herein, according to a practitioner's preference, and based upon the present disclosure.

The prognostic methods of the invention also are useful for determining a proper course of treatment for a patient having KD. A course of treatment refers to the therapeutic measures taken for a patient after diagnosis or after treatment for KD. For example, after diagnosis of KD, a subject may be treated by administration of high doses of aspirin, or administration of immunoglobulin.

The present invention is also directed to commercial kits for the detection and prognostic evaluation of KD. The kit can be in any configuration well known to those skilled in the art and is useful for performing one or more of the methods described herein for the detection or quantitation of at least one KD biomarker (e.g., filamin B, filamin C, or meprin A). The kits are convenient in that they supply many, if not all, of the essential reagents for conducting an assay for the detection of at least one KD biomarker in a test biological sample (e.g., a urine sample or serum sample), such as described herein. In addition, the assay may be performed simultaneously with a standard or multiple standards included in the kit, such as a predetermined amount of at least one KD biomarker, so that the results of the test can be quantified or validated.

In a particular embodiment, the kit comprises a means for detecting levels of at least one KD biomarker in a sample of urine. The kit may comprise a "dipstick" with at least one KD biomarker binding agent immobilized thereon, which specifically binds a KD biomarker protein. Specifically bound KD biomarker can then be detected using, for example, a second antibody that is detectably labeled with a colorimetric agent or radioisotope.

In other embodiments, the assay kits may contain components for competitive and non-competitive assays, radioimmunoassay (RIA), multiplex bead assays, bioluminescence and chemiluminescence assays, fluorometric assays, sandwich assays, immunoradiometric assays, dot blots, enzyme linked assays including ELISA, microtiter plates, or immunocytochemistry. For each kit the range, sensitivity, precision, reliability, specificity, and reproducibility of the assay are established by means well known to those skilled in the art.

Other aspects of the invention provide methods for monitoring or improving the efficacy of treatment for KD, by determining the levels of at least one KD biomarker (e.g., filamin B, filamin C, or meprin A).

Accordingly, in one embodiment of this aspect, the method comprises (a) measuring a level (e.g., quantity or concentration) of at least one biomarker in a panel of biomarkers comprising meprin A, filamin B, or filamin C; and (b) comparing the level of the at least one biomarker with a reference level of the at least one biomarker, wherein an increase in the level of at least one biomarker in the sample relative to the reference level indicates a need to administer to the subject a therapeutic treatment for KD. In some embodiments, the biological sample is a urine sample. In some embodiments, the biological sample is a serum sample.

In another embodiment of this aspect, the method comprises contacting a biological sample obtained from a subject with at least one agent specific for at least one biomarker in a panel of biomarkers comprising meprin A, filamin B, or filamin C; (b) measuring the level of the biomarker using an assay specific for the at least one agent; and (c) comparing the level of the biomarker with a reference level of the biomarker, wherein an increase in the level of the biomarker in the sample relative to the reference level of the biomarker indicates a need to administer to the subject a therapeutic treatment for KD. In some embodiments, the biological sample is a urine sample. In some embodiments, the biological sample is a serum sample.

In another embodiment of this aspect, a method for monitoring treatment efficacy of a subject with KD is provided, the method comprising: (a) determining, from a biological sample obtained from a subject at a first time point, a level (e.g., amount or concentration) of at least one biomarker in a panel of biomarkers comprising meprin A, filamin B, or filamin C; (b) determining a level of said biomarker from a sample obtained from the subject at a second time point; and (c) comparing the level of the biomarker at the second time point with the level of the biomarker in a at the first time point, wherein a decrease in the level or concentration of the at least one biomarker at said second time point indicates the treatment is efficacious for said subject, and wherein an increase in the level or concentration of the at least one biomarker at said second time point indicates the treatment is not efficacious for said subject. In some embodiments, the biological sample is a urine sample. In some embodiments, the biological sample is a serum sample.

The efficacy of a given treatment for KD can be determined by the skilled clinician, for example, using the criteria discussed herein. Treatment can include, for example, administration of high doses of aspirin or administration to intravenous immunoglobulin. An "effective amount" of a KD treatment is a sufficient amount of the treatment to lessen, alleviate, or resolve KD or KD symptoms at least for some period of time, i.e., temporarily if not permanently.

The present invention therefore provides for systems (e.g., comprising computer readable media for causing computer systems) to perform methods for assessing whether an individual has KD. Hence, another aspect relates to a computer readable storage medium having computer readable instructions recorded thereon to define software modules for implementing on a computer a method for diagnosing KD of at least one individual, the computer readable storage medium comprising: (a) instructions for storing and accessing data representing a level of at least one biomarker and a level of a normalizing protein determined for a biological sample obtained from at least one individual; (b) instructions for normalizing the level of the at least one biomarker to the level of normalizing protein via a normalization module, thereby producing a normalized level of the at least one biomarker, (c) instructions for comparing the normalized level of the at least one biomarker with reference data stored on the storage device using a comparison module, wherein the comparing step produces a retrieved content, and (d) instructions for displaying a page of the retrieved content for the user, wherein the retrieved content displays if there is a change in the normalized level of the at least one biomarker, thereby determining whether the at least one individual has KD. In one embodiment, the normalizing protein is total protein. In one embodiment, the biological sample is a urine sample. In one embodiment, the biological sample is serum.

An alternative embodiment includes a computer system for obtaining data from a biological sample obtained from at least one individual, the system comprising: (a) a specimen container to hold a biological sample; (b) a determination module configured to determine reporter molecule information, wherein the reporter molecule information comprises (1) information representing binding of an agent to a normalizing protein, and (2) information representing binding of an agent to at least one biomarker; (c) a storage device configured to store data output from the determination module; (d) a normalization module configured to normalize reporter molecule information representing binding of an agent to at least one biomarker to reporter molecule information representing binding of an agent to normalizing protein; (e) a comparison module adapted to compare the data obtained from the normalization module with reference data on the storage device, wherein the comparison module produces a retrieved content; and (f) a display module for displaying a page of the retrieved content for the user, wherein the retrieved content displays if there is a change in the normalized level of the biomarker, thereby determining whether the individual has KD. In one embodiment, the normalizing protein is a specific protein. In one embodiment, the normalizing protein is total protein. In one embodiment, the biological sample is a urine sample. In another embodiment, the biological sample is serum.

Systems and computer readable media described herein are merely illustrative embodiments of the invention for performing methods of assessing whether an individual has a chronic kidney injury, and are not intended to limit the scope of the invention. The modules of the machine, or those used in the computer readable medium, may assume numerous configurations. For example, function may be provided on a single machine or distributed over multiple machines. Variations of the systems and computer readable media described herein are possible and are intended to fall within the scope of the invention.

The aspects and embodiments of the present invention provide for the first validated diagnostic biomarkers for KD; compositions, kits and methods for accurate, rapid, and low/non-invasive test(s), and analytical and point-of-care test(s) for emergency care departments, hospital- and office-based physicians. The aspects and embodiments of the present invention are advantageous in accuracy and timeliness of evaluations that may curtail unnecessary hospitalizations, treatments or procedures, through low-cost, widespread incorporate into clinical practice.

EXAMPLES

Example 1. Study Design, Participants, and Outcomes

A study was conducted in two phases. For the discovery phase, urine samples from six patients with KD, including both patients with and without coronary artery ectasia, were compared with urine samples from six patients initially suspected of KD but with the final diagnosis of febrile illnesses mimicking KD. The discovery analysis also included three intra-individual control specimens collected from patients with KD after completing treatment and resolution of symptoms. The validation phase enrolled patients evaluated for possible KD, but before the determination of the final diagnosis. Serum specimens collected from an independent validation cohort collected as part of the Pediatric Heart Network Study of Kawasaki disease. See Newburger et al., 356 New Engl. J. Med. 663 (2007).

For all study patients, urine was collected as clean-catch samples. Specimens were labeled with a study number such that all analysis was blinded. Specimens were stored at −80° C. within 6 hr of collection. Blood specimens for serum collection were clotted and centrifuged according to standard methods, with the serum stored at −80° C. within 30 min of collection.

The study was conducted at a tertiary care pediatric hospital and approved by the Children's Hospital Boston Committee on Clinical Investigation. Patients younger than 18 years of age who were being evaluated for possible KD were enrolled according to clinical history and physical examination. Eligible patients had at least 4 days of fever and either four or more principal clinical criteria for KD (Newburger et al., 110 Circulation 2747 (2004)), or a coronary artery z-score of 2.5 or more for the proximal right coronary artery or the left anterior descending coronary artery, as measured by two-dimensional echocardiography. In addition, patients with incomplete presentations of KD meeting only three diagnostic clinical criteria were enrolled based on expert opinion. Patients were excluded if they had pre-existing neoplastic, renal or urologic disease or were pregnant. The pediatric emergency medicine or rheumatology physicians obtained written consent from caregivers and assent for children older than 7 years of age.

Final diagnosis was determined by pediatric rheumatology physicians of a single tertiary care institution according to published diagnostic criteria for KD. Newberger et al., 2004. For patients enrolled as part of the Pediatric Heart Network Study, the final diagnosis was determined using identical criteria. Newburger et al., 356 New Engl. J. Med. 663 (2007). For patients who were not hospitalized, the outcome was confirmed by telephone 6-8 weeks after evaluation using scripted questions or from medical chart review to ascertain whether the patient had any subsequent medical care. For patients who were found to not have KD, a diagnosis of non-specific viral syndrome was assigned based on clinical evaluation, if no specific pathogen was identified. All studied patients received a final outcome. Clinical and laboratory data was tracked using standardized case report forms.

Example 2. Urine Proteome Analysis and Immunoassays

For the discovery of candidate markers of KD, thawed 5 ml urine aliquots were fractionated using ultracentrifugation, protein precipitation, SDS-polyacrylamide gel electrophoresis, and reverse-phase liquid chromatography, as published in detail. Kentsis et al., 3 Proteomics Clin. Appl. 1052 (2009). Individual urine protein fractions were subjected to liquid chromatography tandem mass spectrometry using a nanoflow HPLC system (Eksigent, Dublin, Calif.) coupled to the hybrid linear ion trap-Fourier transform ion cyclotron resonance mass spectrometer (LTQ FT Ultra, Thermo Scientific, Waltham, Mass.). For each MS/MS spectrum, the 200 most intense peaks were extracted, and searched against the human International Protein Index database (version 3.69, internet website of ebi period ac period uk) by using MASCOT (version 2.1.04, Matrix Science). Assessment of identification accuracy was carried out by searching a decoy database composed of reversed protein sequences of the target IPI database. Elias & Gygi, 4 Nat Methods 207 (2007). Only proteins identified on the basis of two or more unique peptides were included in the analysis, at a false discovery rate of less than 1% at the peptide level. Analyzed individual urine proteomes are openly available at the Proteome Commons (http://proteomecommons.org). In addition to filamin B, filamin C, and meprin A, an additional marker indicated in Table 51 may be of use in the diagnosis of KD.

Concentrations of filamin C and meprin A were measured using enzyme-linked immunosorbent assays (USCN Life Science, Wuhan, China). The lowest detection limits of the assays were 0.1 ng/ml and 0.06 ng/ml, respectively, with the coefficient of variation for the quality control specimens of less than 10% for both assays.

Statistical Analysis: Discovery urine proteomes were assembled by parsimonious protein grouping, as described (Kentsis et al., 2009), with the individual peptide counts summed to calculate protein spectral counts. Bayesian statistics, as implemented in QSpec (Choi et al., 7 Mol. Cell. Proteomics 2373 (2008)), were used to analyze normalized protein spectral counts to identify proteins that are statistically significantly enriched in samples from patients with Kawasaki disease, but not in samples from non-Kawasaki disease patients or intra-personal control samples of patients with Kawasaki disease after completion of treatment. Receiver operating characteristics and multivariate linear regression models were calculated using standard methods (STATA, version 10.1, StataCorp). All statistical tests were two-tailed using comparisons of log-transformed measurements.

TABLE S1

Proteins identified uniquely in the urine of patients with Kawasaki disease

| IPI ID | UniProt/SwissProt ID | HGNC symbol | Description [source HGNC Symbol unless noted] |
|---|---|---|---|
| IPI00062003 | | ACAT1 | acetyl-CoA acetyltransferase 1 [Acc: 93] |
| IPI00414057 | | ACTA1 | actin, alpha 1, skeletal muscle [HGNC Symbol; Acc: 129] |
| IPI00759776 | | ACTN1 | actinin, alpha 1 [Acc: 163] |
| IPI00019884 | ACTN2_HUMAN | ACTN2 | actinin, alpha 2 [Acc: 164] |
| IPI00183703 | | AMICA1 | adhesion molecule, interacts with CXADR antigen 1 [Acc: 19084] |
| IPI00020019 | ADIPO_HUMAN | ADIPOQ | adiponectin, C1Q and collagen domain containing [Acc: 13633] |
| IPI00029733 | AK1C1_HUMAN | AKR1C1 | aldo-keto reductase family 1, member C1 (dihydrodiol dehydrogenase 1; 20-α(3-α)-hydroxysteroid dehydrogenase) [Acc: 384] |
| IPI00293721 | ARK73_HUMAN | AKR7A3 | aldo-keto reductase family 7, member A3 (aflatoxin aldehyde reductase) [Acc: 390] |
| IPI00298622 | PPBI_HUMAN | ALPI | alkaline phosphatase, intestinal [Acc: 437] |
| IPI00816309 | ZA2G_HUMAN | AZGP1 | alpha-2-glycoprotein 1, zinc-binding [Acc: 910] |
| IPI00042580 | APOO_HUMAN | APOO | apolipoprotein O [Acc: 28727] |
| IPI00007068 | ARP3B_HUMAN | ACTR3B | ARP3 actin-related protein 3 homolog B (yeast) [Acc: 17256] |
| IPI00298306 | ATM_HUMAN | ATM | ataxia telangiectasia mutated [Acc: 795] |
| IPI00186972 | | AGBL5 | ATP/GTP binding protein-like 5 [Acc: 26147] |
| IPI00302644 | | ATP6V1C2 | ATPase, H+ transporting, lysosomal 42kDa, V1 subunit C2 [Acc: 18264] |
| IPI00003021 | AT1A2_HUMAN | ATP1A2 | ATPase, Na+/K+ transporting, α2 polypeptide [Acc: 800] |
| IPI00293460 | ABCA1_HUMAN | ABCA1 | ATP-binding cassette, sub-family A (ABC1), member 1 [Acc: 29] |
| IPI00019906 | | BSG | basigin (Ok blood group) [Acc: 1116] |
| IPI00744685 | | BTD | biotinidase [Acc: 1122] |
| IPI00254408 | | BPTF | bromodomain PHD finger transcription factor [Acc: 3581] |
| IPI00290089 | CAD17_HUMAN | CDH17 | cadherin 17, LI cadherin (liver-intestine) [Acc: 1756] |
| IPI00020599 | CALR_HUMAN | CALR | calreticulin [Acc: 1455] |
| IPI00026185 | CAPZB_HUMAN | CAPZB | capping protein (actin filament) muscle Z-line, β[Acc: 1491] |
| IPI00009823 | CBPA1_HUMAN | CPA1 | carboxypeptidase A1 (pancreatic) [2296] |
| IPI00009826 | CBPB1_HUMAN | CPB1 | carboxypeptidase B1 (tissue) [Acc: 2299] |
| IPI00385428 | | CEACAM1 | carcinoembryonic antigen-related cell adhesion molecule 1 (biliary glycoprotein) [Acc: 1814] |
| IPI00027412 | CEAM6_HUMAN | CEACAM6 | carcinoembryonic antigen-related cell adhesion molecule 6 (non-specific cross reacting antigen) [Acc: 1818] |
| IPI00658053 | CATD_HUMAN | CTSD | cathepsin D [Acc: 2529] |
| IPI00299150 | CATS_HUMAN | CTSS | cathepsin S [Acc: 2545] |
| IPI00385291 | | CD82 | CD82 molecule [Acc: 6210] |
| IPI00477763 | MRCKB_HUMAN | CDC42BPB | CDC42 binding protein kinase beta (DMPK-like) [Acc: 1738] |
| IPI00009619 | | CADM3 | cell adhesion molecule 3 [Acc: 17601] |
| IPI00413781 | | CXCL12 | chemokine (C-X-C motif) ligand 12 [Acc: 10672] |
| IPI00014625 | CLCA1_HUMAN | CLCA1 | chloride channel accessory 1 [Acc: 2015] |
| IPI00298082 | CLCA4_HUMAN | CLCA4 | chloride channel accessory 4 [Acc: 2018] |
| IPI00307485 | CEL3B_HUMAN | CELA3B | chymotrypsin-like elastase family, member 3B [Acc: 15945] |
| IPI00642792 | CNDP2_HUMAN | CNDP2 | CNDP dipeptidase 2 (metallopeptidase M20 family) [Acc: 24437] |
| IPI00413344 | COF2_HUMAN | CFL2 | cofilin 2 (muscle) [Acc: 1875] |
| IPI00743696 | CO4A1_HUMAN | COL4A1 | collagen, type IV, α1 [Acc: 2202] |
| IPI00021715 | CO4A5_HUMAN | COL4A5 | collagen, type IV, α5 [Acc: 2207] |
| IPI00329573 | COCA1_HUMAN | COL12A1 | collagen, type XII, α1 [Acc: 2188] |
| IPI00472110 | CR1L_HUMAN | CR1L | complement component (3b/4b) receptor 1-like [Acc: 2335] |
| IPI00332395 | CPNE9_HUMAN | CPNE9 | copine family member IX [Acc: 24336] |
| IPI00002657 | CPNE7_HUMAN | CPNE7 | copine VII [Acc: 2320] |
| IPI00377041 | CSMD3_HUMAN | CSMD3 | CUB and Sushi multiple domains 3 [Acc: 19291] |
| IPI00249672 | CUZD1_HUMAN | CUZD1 | CUB and zona pellucida-like domains 1 [Acc: 17937] |
| IPI00216569 | CYTF_HUMAN | CST7 | cystatin F (leukocystatin) [Source:HGNC Symbol;Acc: 2479] |
| IPI00176698 | CYC_HUMAN | CYCS | cytochrome c, somatic [Source:HGNC Symbol;Acc: 19986] |
| IPI00071824 | CKAP2_HUMAN | CKAP2 | cytoskeleton associated protein 2 [Acc: 1990] |
| IPI00376377 | DHRS2_HUMAN | DHRS2 | dehydrogenase/reductase (SDR family) member 2 [Acc: 18349] |
| IPI00418512 | DMBT1_HUMAN | DMBT1 | deleted in malignant brain tumors 1 [Acc: 2926] |
| IPI00028931 | DSG2_HUMAN | DSG2 | desmoglein 2 [Acc: 3049] |
| IPI00007249 | ENPP4_HUMAN | ENPP4 | ectonucleotide pyrophosphatase/phosphodiesterase 4 (putative) [Acc: 3359] |
| IPI00006690 | PERE_HUMAN | EPX | eosinophil peroxidase [Acc: 3423] |
| IPI00419721 | EPMIP_HUMAN | EPM2AIP1 | EPM2A (laforin) interacting protein 1 [Acc: 19735] |
| IPI00376221 | E41L5_HUMAN | EPB41L5 | erythrocyte membrane protein band 4.1 like 5 [Acc: 19819] |
| IPI00025491 | IF4A1_HUMAN | EIF4A1 | eukaryotic translation initiation factor 4A1 [Acc: 3282] |

TABLE S1-continued

Proteins identified uniquely in the urine of patients with Kawasaki disease

| IPI ID | UniProt/SwissProt ID | HGNC symbol | Description [source HGNC Symbol unless noted] |
|---|---|---|---|
| IPI00010105 | IF6_HUMAN | EIF6 | eukaryotic translation initiation factor 6 [Acc: 6159] |
| IPI00064917 | | FAM151A | family with sequence similarity 151, member A [Acc: 25032] |
| IPI00554521 | FRIH_HUMAN | FTH1 | ferritin, heavy polypeptide 1 [Acc: 3976] |
| IPI00339224 | | FN1 | fibronectin 1 [Acc: 3778] |
| IPI00289334 | FLNB_HUMAN | FLNB | filamin B, β[Acc: 3755] |
| IPI00178352 | FLNC_HUMAN | FLNC | filamin C, γ[Acc: 3756] |
| IPI00031708 | FAAA_HUMAN | FAH | fumarylacetoacetate hydrolase (fumarylacetoacetase) [Acc: 3579] |
| IPI00298383 | | FXYD2 | FXYD domain containing ion transport regulator 2 [Acc: 4026] |
| IPI00019383 | GALK1_HUMAN | GALK1 | galactokinase 1 [Acc: 4118] |
| IPI00441550 | | GLB1 | galactosidase, β1 [Acc: 4298] |
| IPI00098026 | | GGT1 | gamma-glutamyltransferase 1 [Acc: 4250] |
| IPI00018169 | IF_HUMAN | GIF | gastric intrinsic factor (vitamin B synthesis) [Acc: 4268] |
| IPI00513929 | | GDI2 | GDP dissociation inhibitor 2 [Acc: 4227] |
| IPI00003929 | GSTA3_HUMAN | GSTA3 | glutathione S-transferase α3 [Acc: 4628] |
| IPI00639805 | | GSTM2 | glutathione S-transferase μ2 (muscle) [Acc: 4634] |
| IPI00795622 | | GAPDH | glyceraldehyde-3-phosphate dehydrogenase [Acc: 4141] |
| IPI00470823 | GP2_HUMAN | GP2 | glycoprotein 2 (zymogen granule membrane) [Acc: 4441] |
| IPI00640867 | | GNAS | GNAS complex locus [Acc: 4392] |
| IPI00306543 | GDF15_HUMAN | GDF15 | growth differentiation factor 15 [Acc: 30142] |
| IPI00249267 | H2AZ_HUMAN | H2AFZ | H2A histone family, member Z [Acc: 4741] |
| IPI00419884 | H3C_HUMAN | H3F3C | H3 histone, family 3C [Acc: 33164] |
| IPI00009931 | HDHD3_HUMAN | HDHD3 | haloacid dehalogenase-like hydrolase domain containing 3 [Acc: 28171] |
| IPI00657660 | | HBD | hemoglobin, δ [Acc: 4829] |
| IPI00641229 | IGHA2_HUMAN | IGHA2 | immunoglobulin heavy constant α2 (A2m marker) [Acc: 5479] |
| IPI00553092 | | IGLV7-46 | immunoglobulin lambda variable 7-46 (gene/pseudogene) [Acc: 5930] |
| IPI00103356 | | ITGB2 | integrin, β2 (complement component 3 receptor 3 & 4 subunit) [Acc: 6155] |
| IPI00103436 | ITLN2_HUMAN | ITLN2 | intelectin 2 [Acc: 20599] |
| IPI00011692 | INVO_HUMAN | IVL | involucrin [Acc: 6187] |
| IPI00166646 | JPH3_HUMAN | JPH3 | junctophilin 3 [Acc: 14203] |
| IPI00001639 | IMB1_HUMAN | KPNB1 | karyopherin (importin) β1 [Acc: 6400] |
| IPI00216136 | | KHK | ketohexokinase (fructokinase) [Acc:6315] |
| IPI00448751 | | KIAA1598 | KIAA1598 [Acc:29319] |
| IPI00604711 | KIF1A_HUMAN | KIF1A | kinesin family member 1A [Acc:888] |
| IPI00554498 | LDHC_HUMAN | LDHC | lactate dehydrogenase C [Acc: 6544] |
| IPI00016670 | LTOR1_HUMAN | LAMTOR1 | late endosomal/lysosomal adaptor, MAPK & MTOR activator 1 [Acc: 26068] |
| IPI00009750 | LEG4_HUMAN | LGALS4 | lectin, galactoside-binding, soluble, 4 [Acc: 6565] |
| IPI00788236 | LAIR1_HUMAN | LAIR1 | leukocyte-associated immunoglobulin-like receptor 1 [Acc: 6477] |
| IPI00017940 | LMBD2_HUMAN | LMBRD2 | LMBR1 domain containing 2 [Acc: 25287] |
| IPI00472013 | 1A31_HUMAN | HLA-A | major histocompatibility complex, class I, A [Acc: 4931] |
| IPI00743503 | 1A26_HUMAN | HLA-A | major histocompatibility complex, class I, A [Acc: 4931] |
| IPI00472057 | 1B73_HUMAN | HLA-B | major histocompatibility complex, class I, B [Acc: 4932] |
| IPI00015988 | HLAG_HUMAN | HLA-G | major histocompatibility complex, class I, G [Acc: 4964] |
| IPI00013400 | MMP7_HUMAN | MMP7 | matrix metallopeptidase 7 (matrilysin, uterine) [Acc: 7174] |
| IPI00167941 | MDN1_HUMAN | MDN1 | MDN1, midasin homolog (yeast) [Acc: 18302] |
| IPI00004372 | MEP1A_HUMAN | MEP1A | meprin A, α (PABA peptide hydrolase) [Acc: 7015] |
| IPI00178015 | MEP1B_HUMAN | MEP1B | meprin A, β [Acc: 7020] |
| IPI00103065 | MITD1_HUMAN | MITD1 | MIT, microtubule interacting & transport, domain containing 1 [Acc: 25207] |
| IPI00418221 | M3K6_HUMAN | MAP3K6 | mitogen-activated protein kinase kinase kinase 6 [Acc: 6858] |
| IPI00027201 | MUC2_HUMAN | MUC2 | mucin 2, oligomeric mucus/gel-forming [Acc: 7512] |
| IPI00028553 | | MINPP1 | multiple inositol-polyphosphate phosphatase 1 [Acc: 7102] |
| IPI00019190 | MYOC_HUMAN | MYOC | myocilin, trabecular meshwork inducible glucocorticoid response [Acc: 7610] |
| IPI00217493 | MYG_HUMAN | MB | myoglobin [Source:HGNC Symbol;Acc: 6915] |
| IPI00844172 | | MYO6 | myosin VI [Acc: 7605] |
| IPI00023152 | NALDL_HUMAN | NAALADL1 | N-acetylated α-linked acidic dipeptidase-like 1 [Acc: 23536] |
| IPI00220059 | NDUB4_HUMAN | NDUFB4 | NADH dehydrogenase (ubiquinone) 1β subcomplex, 4, 15kDa [Acc: 7699] |
| IPI00009253 | SNAA_HUMAN | NAPA | N-ethylmaleimide-sensitive factor attachment protein, α[Acc: 7641] |
| IPI00514877 | | NCSTN | nicastrin [Acc: 17091] |
| IPI00337541 | NNTM_HUMAN | NNT | nicotinamide nucleotide transhydrogenase [Acc: 7863] |
| IPI00451429 | | NIF3L1 | NIF3 NGG1 interacting factor 3-like 1 (*S pombe*) [Acc: 13390] |
| IPI00017304 | NOS2_HUMAN | NOS2 | nitric oxide synthase 2, inducible [Acc: 7873] |
| IPI00290416 | OLA1_HUMAN | OLA1 | Obg-like ATPase 1 [Acc: 28833] |
| IPI00742748 | OBSCN_HUMAN | OBSCN | obscurin, cytoskeletal calmodulin & titin-interacting RhoGEF [Acc: 15719] |
| IPI00022324 | O2AG1_HUMAN | OR2AG1 | olfactory receptor, family 2, subfamily AG, member 1 [Acc: 15142] |
| IPI00027720 | LIPP_HUMAN | PNLIP | pancreatic lipase [Acc: 9155] |
| IPI00016387 | PCF11_HUMAN | PCF11 | PCF11, cleavage and polyadenylation factor subunit, homolog (*S. cerevisiae*) [Acc: 30097] |

TABLE S1-continued

Proteins identified uniquely in the urine of patients with Kawasaki disease

| IPI ID | UniProt/SwissProt ID | HGNC symbol | Description [source HGNC Symbol unless noted] |
|---|---|---|---|
| IPI00641498 | PDZ1P_HUMAN | PDZK1 | PDZ domain containing 1 [Acc: 8821] |
| IPI00641244 | | PRDX1 | peroxiredoxin 1 [Acc: 9352] |
| IPI00219568 | PGK2_HUMAN | PGK2 | phosphoglycerate kinase 2 [Acc: 8898] |
| IPI00021792 | PA21B_HUMAN | PLA2G1B | phospholipase A2, group IB (pancreas) [Acc: 9030] |
| IPI00026962 | PA2GA_HUMAN | PLA2G2A | phospholipase A2, group IIA (platelets, synovial fluid) [Source:HGNC Symbol;Acc: 9031] |
| IPI00432412 | | | phospholipase inhibitor precursor [Source:RefSeq peptide;Acc: NP_001078943] |
| IPI00789401 | PLSI_HUMAN | PLS1 | plastin 1 [Acc: 9090] |
| IPI00007248 | PKHA6_HUMAN | PLEKHA6 | pleckstrin homology domain containing, family A member 6 [Acc: 17053] |
| IPI00107555 | | PFN2 | profilin 2 [Source:HGNC Symbol;Acc: 8882] |
| IPI00022213 | PEPC_HUMAN | PGC | progastricsin (pepsinogen C) [Acc: 8890] |
| IPI00792533 | | PGC | progastricsin (pepsinogen C) [Acc: 8890] |
| IPI00514208 | | PTGDS | prostaglandin D2 synthase 21kDa (brain) [Acc: 9592] |
| IPI00299571 | | PDIA6 | protein disulfide isomerase family A, member 6 [Acc: 30168] |
| IPI00010466 | KPCB_HUMAN | PRKCB | protein kinase C, β [Acc: 9395] |
| IPI00296337 | PRKDC_HUMAN | PRKDC | protein kinase, DNA-activated, catalytic polypeptide [Acc: 9413] |
| IPI00332271 | PTPRS_HUMAN | PTPRS | protein tyrosine phosphatase, receptor type, S [Acc: 9681] |
| IPI00290350 | | PCDH19 | protocadherin 19 [Acc: 14270] |
| IPI00169326 | PPTC7_HUMAN | PPTC7 | PTC1 protein phosphatase homolog (*S. cerevisiae*) [Acc: 30695] |
| IPI00293327 | P2RX4_HUMAN | P2RX4 | purinergic receptor P2X, ligand-gated ion channel, 4 [Acc: 8535] |
| IPI00442204 | MGAL1_HUMAN | | Putative maltase-glucoamylase-like protein F1116351 [Source:UniProtKB/Swiss-Prot;Acc: Q6ZN80] |
| IPI00024282 | RAB8B_HUMAN | RAB8B | RAB8B, member RAS oncogene family [Acc: 30273] |
| IPI00166044 | RPTOR_HUMAN | RPTOR | regulatory associated protein of MTOR, complex 1 [Acc: 30287] |
| IPI00012622 | RHG20_HUMAN | ARHGAP20 | Rho GTPase activating protein 20 [Acc: 18357] |
| IPI00152023 | RNS11_HUMAN | RNASE11 | ribonuclease, RNase A family, 11 (non-active) [Acc: 19269] |
| IPI00219153 | RL22_HUMAN | RPL22 | ribosomal protein L22 [Acc: 10315] |
| IPI00030179 | RL7_HUMAN | RPL7 | ribosomal protein L7 [Acc: 10363] |
| IPI00745789 | RSSA_HUMAN | RPSA | ribosomal protein SA [Acc: 6502] |
| IPI00171771 | RFWD2_HUMAN | RFWD2 | ring finger & WD repeat domain 2 [Acc: 17440] |
| IPI00433279 | SLFN5_HUMAN | SLFN5 | schlafen family member 5 [Acc: 28286] |
| IPI00002606 | ADSV_HUMAN | SCIN | scinderin [Acc: 21695] |
| IPI00030385 | SBP1_HUMAN | SELENBP1 | selenium binding protein 1 [Acc: 10719] |
| IPI00033583 | SPB12_HUMAN | SERPINB12 | serpin peptidase inhibitor, clade B (ovalbumin), member 12 [Acc: 14220] |
| IPI00307466 | | SERPINB3 | serpin peptidase inhibitor, clade B (ovalbumin), member 3 [Acc: 10569] |
| IPI00413451 | SPB6_HUMAN | SERPINB6 | serpin peptidase inhibitor, clade B (ovalbumin), member 6 [Acc: 8950] |
| IPI00394753 | NRAM2_HUMAN | SLC11A2 | solute carrier family 11 (proton-coupled divalent metal ion transporters), member 2 [Acc: 10908] |
| IPI00008616 | S12A7_HUMAN | SLC12A7 | solute carrier family 12 (potassium/chloride transporters), member 7 [Acc: 10915] |
| IPI00011981 | S13A2_HUMAN | SLC13A2 | solute carrier family 13 (sodium-dependent dicarboxylate transporter), member 2 [Acc: 10917] |
| IPI00020542 | S22AB_HUMAN | SLC22A11 | solute carrier family 22 (organic anion/urate transporter), member 11 [Acc: 18120] |
| IPI00171334 | S22A4_HUMAN | SLC22A4 | solute carrier family 22 (organic cation/ergothioneine transporter), member 4 [Acc: 10968] |
| IPI00029268 | SLC31_HUMAN | SLC3A1 | solute carrier family 3 (cystine, dibasic & neutral amino acid transporters, activator of cystine, dibasic & neutral amino acid transport), member 1 [Acc: 11025] |
| IPI00024248 | SC5A5_HUMAN | SLC5A5 | solute carrier family 5 (sodium iodide symporter), member 5 [Acc: 11040] |
| IPI00760881 | SC5AC_HUMAN | SLC5A12 | solute carrier family 5 (sodium/glucose cotransporter), member 12 [Acc: 28750] |
| IPI00003527 | NHRF1_HUMAN | SLC9A3R1 | solute carrier family 9 (sodium/hydrogen exchanger), member 3 regulator 1 [Acc: 11075] |
| IPI00217882 | SORT_HUMAN | SORT1 | sortilin 1 [Acc: 11186] |
| IPI00657938 | | SNX18 | sorting nexin 18 [Acc: 19245] |
| IPI00178767 | ASM3A_HUMAN | SMPDL3A | sphingomyelin phosphodiesterase, acid-like 3A [Acc: 17389] |
| IPI00291643 | SPRY4_HUMAN | SPRYD4 | SPRY domain containing 4 [Acc: 27468] |
| IPI00000001 | STAU1_HUMAN | STAU1 | staufen, RNA binding protein, homolog 1 (*Drosophila*) [Acc: 11370] |
| IPI00719690 | SAM9L_HUMAN | SAMD9L | sterile α motif domain containing 9-like [Acc: 1349] |
| IPI00514755 | | SDF4 | stromal cell derived factor 4 [Acc: 24188] |
| IPI00032826 | ST134_HUMAN | ST13 | suppression of tumorigenicity 13 (colon carcinoma) (Hsp70 interacting protein) [Acc: 11343] |
| IPI00335277 | SYPL1_HUMAN | SYPL1 | synaptophysin-like 1 [Acc: 11507] |
| IPI00289876 | STX7_HUMAN | STX7 | syntaxin 7 [Acc: 11442] |
| IPI00642310 | | STXBP2 | syntaxin binding protein 2 [Acc: 11445] |
| IPI00298994 | TLN1_HUMAN | TLN1 | talin 1 [Acc: 11845] |

TABLE S1-continued

Proteins identified uniquely in the urine of patients with Kawasaki disease

| IPI ID | UniProt/SwissProt ID | HGNC symbol | Description [source HGNC Symbol unless noted] |
|---|---|---|---|
| IPI00183938 | TTC27_HUMAN | TTC27 | tetratricopeptide repeat domain 27 [Acc: 25986] |
| IPI00290452 | TMBI1_HUMAN | TMBIM1 | transmembrane BAX inhibitor motif containing 1 [Acc: 23410] |
| IPI00023788 | ENTK_HUMAN | TMPRSS15 | transmembrane protease, serine 15 [Acc: 9490] |
| IPI00010252 | TRI33_HUMAN | TRIM33 | tripartite motif containing 33 [Acc: 16290] |
| IPI00018511 | TBB8B_HUMAN | | Tubulin β-8 chain B [Source: UniProtKB/Swiss-Prot;Acc: A6NNZ2] |
| IPI00179709 | TBA3C_HUMAN | TUBA3C | tubulin, α 3c [Acc: 12408] |
| IPI00179709 | TBA3C_HUMAN | TUBA3D | tubulin, α 3d [Acc: 24071] |
| IPI00640721 | 1433B_HUMAN | YWHAB | tyrosine 3-monooxygenase/tryptophan 5-monooxygenase activation protein, β polypeptide [Acc: 12849] |
| IPI00011245 | UBP29_HUMAN | USP29 | ubiquitin specific peptidase 29 [Acc: 18563] |
| IPI00783859 | | VPS13D | vacuolar protein sorting 13 homolog D (*S. cerevisiae*) [Acc: 23595] |
| IPI00031655 | VPS25_HUMAN | VPS25 | vacuolar protein sorting 25 homolog (*S. cerevisiae*) [Acc: 28122] |
| IPI00423568 | RASK_HUMAN | KRAS | v-Ki-ras2 Kirsten rat sarcoma viral oncogene homolog [Acc: 6407] |
| IPI00642108 | | WDR45 | WD repeat domain 45 [Acc: 28912] |
| IPI00550192 | XPP3_HUMAN | XPNPEP3 | X-prolyl aminopeptidase (aminopeptidase P) 3, putative [Acc: 28052] |
| IPI00014513 | TYY1_HUMAN | YY1 | YY1 transcription factor [Acc: 12856] |
| IPI00743220 | ZN561_HUMAN | ZNF561 | zinc finger protein 561 [Acc: 28684] |

Example 3. Murine Model of Coronary Arteritis and Meprin A Immunohistochemistry

An established murine model of coronary arteritis based on intraperitoneal injection of the cell wall extract of group B *Lactobacillus casei* (LCWE) was used. Lehman et al., 48 Clin. Immunol. Immunopathol. 108 (1988). Group B *L. casei* were grown and a cell wall extract (LCWE) was prepared as described. Schulte et al., 183 J. Immunol. 5311 (2009). Briefly, 6-week old C57/BL6 mice were injected with 250 µg of LCWE in phosphate buffered saline (PBS) or with saline alone. Fourteen days later, mice were sacrificed, and coronary arteries were identified in serial sections (7 µm), fixed with formalin, and stained with hematoxylin and eosin. For the immunohistochemical analysis, sections were pre-treated with 0.3% hydrogen peroxide in PBS for 30 min. Meprin A (clone F-20, Santa Cruz Biotech., Santa Cruz, Calif.) or isotype control antibody (goat serum, Santa Cruz Biotech.) was applied in 0.5% bovine serum albumin in PBS at 1:100 for 1 hr. Slides were then washed and biotinylated anti-goat horseradish peroxidase conjugated secondary antibody (Vector Lab, Burlingame, Calif.) was applied at 1:500 for 30 min, washed and stained with streptavidin conjugated horseradish peroxidase (BD Biosciences, San Diego, Calif.) at 1:1,000 for 30 min. Immunohistochemical staining was detected using the SK-4100 DAB kit, as per manufacturer's instructions (Vector Lab).

What is claimed is:

1. A method of treating Kawasaki disease (KD) comprising:
   a) analyzing a biological sample obtained from a subject for an increase in the level of at least one biomarker, selected from meprin A, filamin B, and filamin C, wherein the increase is determined by comparing the level of said biomarker with a reference level, wherein the reference level is the level of the selected biomarker in healthy individuals who do not have KD and wherein the subject presents at least one symptom of KD;
   b) administering a therapeutic treatment comprising immunoglobulin to the subject when the subject has an increase in the selected at least one biomarker tested.

2. The method of claim 1, wherein both meprin A and filamin C are selected.

3. The method of claim 1, wherein the biological sample is urine or serum.

4. The method of claim 1, wherein the level of the biomarker is detected using an antibody-based binding agent which specifically binds to the biomarker.

5. The method of claim 1, wherein the level of said biomarker obtained from the subject and the reference level are normalized prior to the comparison.

6. A method of detecting a biomarker of Kawasaki disease (KD) in a subject suspected of having KD prior to treatment for KD comprising:
   a) selecting a subject who presents at least one symptom of KD; and
   b) analyzing a biological sample obtained from the subject for an increase in the level of at least one biomarker, selected from meprin A, filamin B, and filamin C, wherein the increase is determined by comparing the level of said biomarker with a reference level, wherein the reference level is the level of the selected biomarker in healthy individuals who do not have KD.

7. The method of claim 6, wherein the biological sample is urine or serum.

8. The method of claim 6, wherein the level of the biomarker is detected using an antibody-based binding agent which specifically binds to the biomarker.

9. The method of claim 6, wherein the level of said biomarker obtained from the subject and the reference level are normalized prior to the comparison.

* * * * *

UNITED STATES PATENT AND TRADEMARK OFFICE
CERTIFICATE OF CORRECTION

PATENT NO. : 9,869,673 B2
APPLICATION NO. : 14/111816
DATED : January 16, 2018
INVENTOR(S) : Alex Kentsis et al.

Page 1 of 1

It is certified that error appears in the above-identified patent and that said Letters Patent is hereby corrected as shown below:

In the Specification

At Column 1, Line 17 please delete:
"FEDERAL FUNDING"
And insert the following text:
-- GOVERNMENT SUPPORT --

At Column 1, Lines 19-25 please delete:
"This invention was made, in part, with Federal funding under grants No. U01 HL068285, RR 02172, U01 HL068270, U01 HL068269, U01 HL068292, U01 HL068290, U01 HL068288, U01 HL068281, and U01 HL068279, awarded by the National Institutes of Health. The U.S. Federal Government has certain rights in the invention."
And insert the following text:
-- This invention was made with government support under grant numbers HL068285, RR002172, HL068270, HL068269, HL068290, HL068292, HL068288, HL068279, and HL068281 awarded by the National Institutes of Health. The Government has certain rights in the invention. --

Signed and Sealed this
Seventeenth Day of July, 2018

Andrei Iancu
*Director of the United States Patent and Trademark Office*